(12) United States Patent
Gee et al.

(10) Patent No.: US 9,599,622 B2
(45) Date of Patent: Mar. 21, 2017

(54) FLUOROGENIC PH-SENSITIVE DYES AND THEIR METHODS OF USE (II)

(71) Applicant: LIFE TECHNOLOGIES CORPORATION, Carlsbad, CA (US)

(72) Inventors: Kyle Gee, Springfield, OR (US); Upinder Singh, Eugene, OR (US); Aleksey Rukavishnikov, Eugene, OR (US); Daniel Beacham, Eugene, OR (US); Shih-Jung Huang, Eugene, OR (US); Michael Janes, Eugene, OR (US); Wenjun Zhou, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/402,358

(22) PCT Filed: Mar. 14, 2013

(86) PCT No.: PCT/US2013/031637
§ 371 (c)(1),
(2) Date: Nov. 20, 2014

(87) PCT Pub. No.: WO2013/180813
PCT Pub. Date: Dec. 5, 2013

(65) Prior Publication Data
US 2015/0218379 A1  Aug. 6, 2015

Related U.S. Application Data

(60) Provisional application No. 61/653,333, filed on May 30, 2012, provisional application No. 61/653,616, filed on May 31, 2012.

(51) Int. Cl.
| | | |
|---|---|---|
| *C09B 11/24* | (2006.01) | |
| *G01N 33/84* | (2006.01) | |
| *C07D 311/90* | (2006.01) | |
| *G01N 33/58* | (2006.01) | |
| *A61K 49/00* | (2006.01) | |
| *G01N 33/50* | (2006.01) | |

(52) U.S. Cl.
CPC ....... *G01N 33/582* (2013.01); *A61K 49/0041* (2013.01); *C07D 311/90* (2013.01); *C09B 11/24* (2013.01); *G01N 33/5005* (2013.01); *G01N 33/84* (2013.01)

(58) Field of Classification Search
CPC .... C07D 311/90; C09B 11/24; G01N 33/582; G01N 33/84
See application file for complete search history.

(56) References Cited

U.S. PATENT DOCUMENTS

| | | | |
|---|---|---|---|
| 1,885,591 | A | 11/1932 | Coulthard et al. |
| 4,945,171 | A | 7/1990 | Haugland et al. |
| 5,863,727 | A | 1/1999 | Lee et al. |
| 2007/0154926 | A1 | 7/2007 | Lee et al. |
| 2007/0238884 | A1 | 10/2007 | Smith et al. |
| 2008/0254498 | A1 | 10/2008 | Diwu et al. |
| 2008/0274907 | A1 | 11/2008 | Beacham et al. |
| 2009/0004753 | A1 | 1/2009 | Antoulinakis et al. |
| 2015/0218379 | A1 | 8/2015 | Gee et al. |

FOREIGN PATENT DOCUMENTS

| | | |
|---|---|---|
| WO | WO-02/36832 | 5/2002 |
| WO | WO-2005/098437 | 10/2005 |
| WO | WO2013180811 | * 12/2013 |

OTHER PUBLICATIONS

PCT/US2013/031535, , "International Preliminary Report on Patentability and Written Opinion mailed on Dec. 2, 2014", Dec. 2, 2014, 9 Pages.
PCT/US2013/031535, , "International Search Report and Written Opinion", 2013, 13 pgs.
PCT/US2013/031637, , "International Preliminary Report on Patentability", Dec. 11, 2014, 7 pages.
PCT/US2013/031637, , "International Search Report and Written Opinion", 2013, 9 pgs.

* cited by examiner

*Primary Examiner* — Sun Jae Yoo

(57) ABSTRACT

Disclosed herein are compounds, compositions, methods and kits for detecting pH in samples using pH-sensitive fluorescent dyes. The compounds disclosed herein are novel xanthene-derivative dyes comprising an aniline moiety with one or more electron donating groups, which dyes are for detecting pH in samples either in vitro or in vivo. Also described herein are processes for preparing said dyes for use in the disclosed compositions, methods and kits.

20 Claims, 8 Drawing Sheets

A.

B.

EGF Pretreated          Dye-EGF conjugate only

Compound (4) internalization

FLUOROGENIC PH-SENSITIVE DYES AND THEIR METHODS OF USE (II)

CROSS-REFERENCE TO RELATED APPLICATIONS

This application is a 371 national stage application from PCT/US2013/031637, filed Mar. 14, 2013, which claims the benefit of priority to U.S. Provisional Application Ser. No. 61/653,333, filed May 30, 2012 and 61/653,616, filed May 31, 2012, which are herein incorporated by reference in their entirety.

FIELD

Novel pH-sensitive fluorescent dyes and assays for use in a variety of applications including monitoring of intracellular processes are disclosed.

BACKGROUND pH-sensitive fluorescent dyes employed in biological research and medical diagnostics belong to two groups, each distinguished by the origin of fluorescent responses to changes in pH. The first group includes compounds having fluorescence controlled by the ionization of phenolic hydroxyl groups in a fluorophore. Examples include fluorescein, carboxyfluorescein, Oregon Green®, SNARF®, SNAFL®, and HPTS indicators.

U.S. Patent Publication No. 2006/0051874 describes fluorescein-like structures incorporated into a fluorescent detector for monitoring pH of the blood in bank storages. Because the degree of ionization of these types of molecules increases upon lowering the acidity of the environment, they become more fluorescent as pH increases.

Fluorescent pH sensors of the second group include an amino group (aliphatic or aromatic) as an indicator moiety along with a reporter fluorescent dye moiety. When such a molecule absorbs a photon creating an excited electronic state, the electron of the amino group's unshared pair transfers to the orbital vacated by excitation. Such an electron transfer, referred to as Photoinduced Electron Transfer (PET) prevents the excited molecule from emission transition, thus the fluorescence of the dye is quenched. Protonation of the amino group changes the nature and energy of the pair's orbital and stops the PET. As a result, the fluorescent reporter moiety responds to a pH change. Because protonation of the amino group cancels the quenching, the PET-based sensors become more fluorescent as pH decreases.

Examples of PET-based pH sensors include LysoSensor™ dyes, which contain a dimethylamino group as an indicator moiety and CypHer® 5E dye which has an indolenine indicator group. One disadvantage of these sensors is that the working range is shifted to the acidic side because of the low pKa of the indicator amino group.

A family of rhodamine-based pH sensors is described in PCT Publication No. WO 2005/098437 (Smith et al.). The dyes have a benzene ring substituted ortho to the xanthene moiety by —OH or —SH (or their deprotonated forms), such that deprotonation to a negatively charged state quenches the fluorescence and it is only upon protonation of the negatively charged —O⁻ or —S⁻ to a neutral state that the fluorescence is restored. Typically, the pH at which this occurs is less than pH 6. WO 2005/098437 purports that the ionized state of the —OH or —SH group is responsible for the pH response of the dye and that the strong electron withdrawing properties of the tetramethylrhodamine moiety in the dyes significantly decreases the pKa of the indicator group, thus shifting the sensors' working range toward highly acidic pH values. However, this limits the applicability of the dyes described in WO 2005/098437 at a physiological pH (e.g., pH 6-7), especially in biological systems. An additional disadvantage of these dyes is that their pKa is not tunable. Furthermore, these compounds have been found by us to be unstable in solution.

Accordingly, there is a need for additional pH-sensitive fluorescent dyes with improved properties, including in at least some compounds the ability to detect pH changes in biological systems. It is an object of the present invention to develop a novel class of relatively stable fluorescent pH sensors that fluoresce in the red portion of the UV/VIS spectrum, preferably with a working range towards neutral and other biologically relevant pH values that mitigate or remove the disadvantages of the compounds known in art.

SUMMARY

Described herein are compounds, compositions, methods and kits for detecting pH in samples using pH-sensitive fluorescent dyes, which in one aspect, are characterized by the omission of a hydroxyl or thiol group as required by WO 2005/098437. In another aspect, the pH-sensitive fluorescent dyes as disclosed herein allow for the detection of fluorescent responses to changes in pH in the red portion of the UV/VIS spectrum. The present teachings provide a new family of pH-sensitive red fluorescent dyes, having significant and unexpected advantages over existing fluorescent pH-sensors in that the presence of a dialkylamino group para to the alkoxy substituent in the aniline moiety results in physiological pKa values and the pKa's of the dyes provided herein are also tunable. Therefore, the pH-sensitive fluorescent dyes provided herein may be modified to suit a particular application or condition to be analyzed.

In certain embodiments, novel dye compounds are provided for use as fluorescent pH sensors, the dye compounds having structural formula (I):

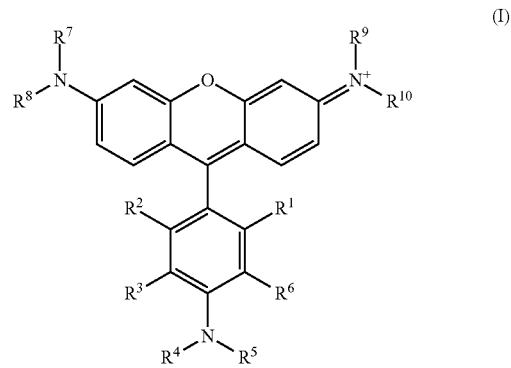

wherein
R¹ is alkoxy or thioalkyl;
R² and R⁶, which may be the same or different, are each independently H, halogen, —ORᵃ, —SRᵃ, —NRᵃRᵇ, or an electron donating group;
R³ is —NR'R'', wherein R' and R'', which may be the same or different, are each independently alkyl or substituted alkyl;

R⁴ is selected from the group consisting of alkyl and substituted alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$, wherein L is a linker, $R_x$ is a reactive group, and $S_c$ is a conjugated substance;

$R^a$ is H, alkyl, or substituted alkyl;

$R^b$ is alkyl or substituted alkyl; and

R⁷, R⁸, R⁹, and R¹⁰, which may be the same or different, are each independently alkyl or alkenyl.

In certain embodiments, R¹-R¹⁰ are as follows:

R¹ is alkoxy or thioalkyl;

R² and R⁶, which may be the same or different, are each independently H or halogen;

R³ is —NR'R", wherein R' and R", which may be the same or different, are each independently alkyl;

R⁴ is alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and R⁷, R⁸, R⁹, and R¹⁰, which may be the same or different, are each independently alkyl or alkenyl.

In certain embodiments, R¹-R¹⁰ are as follows:

R¹ is alkoxy or thioalkyl;

R² and R⁶, which may be the same or different, are each independently H, Cl or F;

R³ is —NR'R", wherein R' and R", which may be the same or different, are each independently alkyl;

R⁴ is alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and R⁷, R⁸, R⁹, and R¹⁰, which may be the same or different, are each independently alkyl or alkenyl.

In certain embodiments, R¹-R¹⁰ are as follows:

R¹ is alkoxy or thioalkyl;

R² and R⁶ are each H;

R³ is —NR'R", wherein R' and R", which may be the same or different, are each independently alkyl;

R⁴ is alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and R⁷, R⁸, R⁹, and R¹⁰, which may be the same or different, are each independently alkyl or alkenyl.

In certain embodiments, R¹-R¹⁰ are as follows:

R¹ is methoxy;

R² and R⁶ are each H;

R³ is —NR'R", wherein R' and R", which may be the same or different, are each independently methyl or ethyl;

R⁴ is methyl or ethyl;

R⁵ is methyl; ethyl; carboxyalkyl; $(CH_2)_nCO(O)R$; $(CH_2)_nC(O)R$; $(CH_2)_nC(O)NHR$; $(CH_2)_nC(O)NRR^c$; wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group selected from carboxyl, carboxylester, amide, maleimide, succinimidyl ester (SE), sulfodichlorophenol (SDP) ester, sulfotetrafluorophenol (STP) ester, tetrafluorophenol (TFP) ester, acetoxymethoxy (AM) ester, nitrilotriacetic acid (NTA), aminodextran, DIBO-amine; -L-$R_x$; or -L-$S_c$; and R⁷, R⁸, R⁹, and R¹⁰, which may be the same or different, are each independently methyl or propenyl.

In certain embodiments, novel dye compounds are provided for use as fluorescent pH sensors, the dye compounds having structural formula (II):

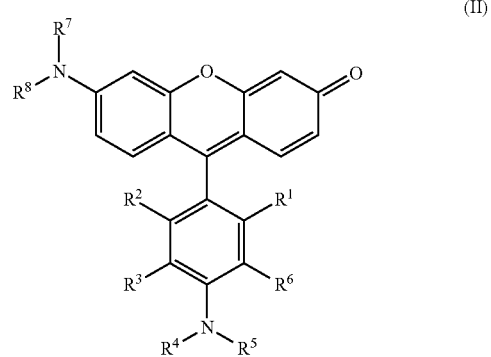

(II)

wherein

R¹ is alkoxy or thioalkyl;

R² and R⁶, which may be the same or different, are each independently H, halogen, —OR$^a$, —SR$^a$, —NR$^a$R$^b$, or an electron donating group;

R³ is —NR'R", wherein R' and R", which may be the same or different, are each independently alkyl or substituted alkyl;

R⁴ is selected from the group consisting of alkyl and substituted alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and R$^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or R$^d$, wherein R$^d$ is $(CH_2)_nC(O)NHR_x$, wherein n is an integer from 1 to 6, and R$_x$ is a reactive group; -L-R$_x$; and -L-S$_c$, wherein L is a linker, R$_x$ is a reactive group, and S$_c$ is a conjugated substance, wherein L is a linker, R$_x$ is a reactive group, and 5, is a conjugated substance;

R$^a$ is H, alkyl, or substituted alkyl;

R$^b$ is alkyl or substituted alkyl; and

R⁷ and R⁸, which may be the same or different, are each independently alkyl or alkenyl.

In certain embodiments, R¹-R⁸ are as follows:

R¹ is alkoxy or thioalkyl;

R² and R⁶, which may be the same or different, are each independently H or halogen;

R³ is —NR'R", wherein R' and R", which may be the same or different, are each independently alkyl;

R⁴ is alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and R$^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or R$^d$, wherein R$^d$ is $(CH_2)_nC(O)NHR_x$, wherein n is an integer from 1 to 6, and R$_x$ is a reactive group; -L-R$_x$; and -L-S$_c$; and R⁷ and R⁸, which may be the same or different, are each independently alkyl or alkenyl.

In certain embodiments, R¹-R⁸ are as follows:

R¹ is alkoxy or thioalkyl;

R² and R⁶, which may be the same or different, are each independently H, Cl or F;

R³ is —NR'R", wherein R' and R", which may be the same or different, are each independently alkyl;

R⁴ is alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and R$^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or R$^d$, wherein R$^d$ is $(CH_2)_nC(O)NHR_x$, wherein n is an integer from 1 to 6, and R$_x$ is a reactive group; -L-R$_x$; and -L-S$_c$; and R⁷ and R⁸, which may be the same or different, are each independently alkyl or alkenyl.

In certain embodiments, R¹-R⁸ are as follows:

R¹ is methoxy;

R² and R⁶ are each H;

R³ is —NR'R", wherein R' and R", which may be the same or different, are each independently methyl or ethyl;

R⁴ is methyl or ethyl;

R⁵ is methyl; ethyl; carboxyalkyl; $(CH_2)_nCO(O)R$; $(CH_2)_nC(O)R$; $(CH_2)_nC(O)NHR$; $(CH_2)_nC(O)NRR^c$; wherein n is an integer from 1 to 6, and R and R$^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or R$^d$, wherein R$^d$ is $(CH_2)_nC(O)NHR_x$, wherein n is an integer from 1 to 6, and R$_x$ is a reactive group selected from carboxyl, carboxylester, amide, maleimide, succinimidyl ester (SE), sulfodichlorophenol (SDP) ester, sulfotetrafluorophenol (STP) ester, tetrafluorophenol (TFP) ester, acetoxymethoxy (AM) ester, nitrilotriacetic acid (NTA), aminodextran, DIBO-amine; -L-R$_x$; or -L-S$_c$;

R⁷ and R⁸, which may be the same or different, are each independently methyl or propenyl.

In certain embodiments, compositions are provided for determining the pH of a sample, the compositions comprising:

a) one or more of the pH-sensitive fluorescent dye compounds described herein; and b) a carrier, wherein the one or more pH-sensitive fluorescent dye compounds are present in an amount effective to detect the pH of the sample.

In certain embodiments, compositions are provided for determining the pH of a sample, the compositions comprising:

(a) one or more of the pH-sensitive fluorescent dye compounds described herein; and (b) an analyte, wherein the one or more pH-sensitive fluorescent dye compounds are present in an amount effective to detect the pH of the sample.

In certain embodiments, methods are provided for determining the pH of a sample, the methods comprising:

(a) contacting the sample with one or more of the pH-sensitive fluorescent dye compounds described herein to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to determine the pH of the sample.

In certain embodiments, methods are provided for determining the pH of a sample, the methods comprising:

(a) contacting the sample with one or more of the compositions described herein to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to determine the pH of the sample.

In certain embodiments, methods are provided for monitoring the pH inside a live cell, the methods comprising:

(a) contacting the cell with one or more of the pH-sensitive fluorescent dye compounds described herein to form a contacted cell;

(b) incubating the contacted cell for a sufficient amount of time for the one or more pH-sensitive fluorescent dye compounds to enter the cell to form a labeled cell;

(c) illuminating the labeled cell with an appropriate wavelength to form an illuminated cell; and (d) detecting fluorescent emissions from the illuminated cell;

wherein the fluorescent emissions are used to monitor the pH inside the cell.

In certain embodiments, methods are provided for monitoring the pH inside a live cell, the methods comprising:

(a) contacting the cell with one or more of the compositions described herein to form a contacted cell;

(b) incubating the contacted cell for a sufficient amount of time for the one or more compositions to enter the cell to form a labeled cell;

(c) illuminating the labeled cell with an appropriate wavelength to form an illuminated cell; and (d) detecting fluorescent emissions from the illuminated cell;

wherein the fluorescent emissions are used to monitor the pH inside the cell.

In certain embodiments, methods are provided for detecting phagocytosis of a carrier molecule in solution, the methods comprising:

(a) conjugating the carrier molecule to one or more of the pH-sensitive fluorescent dye compounds described herein to form a carrier-dye conjugate;

(b) contacting the carrier-dye conjugate with a cell to form a contacted cell;

(c) incubating the contacted cell to form an incubated solution;

(d) illuminating the incubated solution to form an illuminated solution; and (e) detecting fluorescent emissions from the illuminated solution;

wherein fluorescent emissions indicate phagocytosis of the carrier molecule.

In certain embodiments, methods are provided for detecting phagocytosis of a carrier molecule in solution, the methods comprising:

(a) conjugating the carrier molecule to one or more of the compositions described herein to form a carrier-dye conjugate;

(b) contacting the carrier-dye conjugate with a cell to form a contacted cell;

(c) incubating the contacted cell to form an incubated solution;

(d) illuminating the incubated solution to form an illuminated solution; and (e) detecting fluorescent emissions from the illuminated solution;

wherein fluorescent emissions indicate phagocytosis of the carrier molecule.

In certain embodiments, methods are provided for detecting a pH related intracellular process, the methods comprising:

(a) contacting any one of the pH-sensitive fluorescent dye compounds described herein with a cell to form a contacted cell;

(b) incubating the contacted cell to form an incubated solution;

(c) illuminating the incubated solution to form an illuminated solution; and (d) detecting fluorescent emissions from the illuminated solution;

wherein increased fluorescent emissions indicates activation of the intracellular process.

In certain embodiments, methods are provided for detecting a pH related intracellular process, the methods comprising:

(a) contacting any one of the compositions described herein with a cell to form a contacted cell;

(b) incubating the contacted cell to form an incubated solution;

(c) illuminating the incubated solution to form an illuminated solution; and (d) detecting fluorescent emissions from the illuminated solution;

wherein increased fluorescent emissions indicates activation of the intracellular process.

In certain embodiments, methods are provided for identifying a target cell in a population of cells, wherein the target cell is differentially labeled relative to neighboring cells within the population, the methods comprising;

(a) contacting one or more of the pH-sensitive dye compounds disclosed herein with the population of cells to form a contacted cell population;

(b) incubating the contacted cell population for a period of time sufficient for the one or more of the pH-sensitive dye compounds to enter the target cell, thereby forming an incubated cell population; and (c) illuminating the incubated cell population, wherein the target cell is identified by a differential label relative to neighboring cells within the population.

In certain embodiments, methods are provided for identifying a target cell in a population of cells, wherein the target cell is differentially labeled relative to neighboring cells within the population, the methods comprising;

(a) contacting one or more of the compositions disclosed herein with the population of cells to form a contacted cell population;

(b) incubating the contacted cell population for a period of time sufficient for the one or more of the compositions to enter the target cell, thereby forming an incubated cell population; and (c) illuminating the incubated cell population, wherein the target cell is identified by a differential label relative to neighboring cells within the population.

In certain embodiments, methods are provided for diagnosing or detecting a disease in a subject, the method comprising:

(a) contacting a sample obtained from a subject suspected of having the disease with one or more of the pH-sensitive dye compounds disclosed herein to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to diagnose or detect the disease.

In certain embodiments, methods are provided for diagnosing or detecting a disease in a subject, the methods comprising:

(a) contacting a sample obtained from a subject suspected of having the disease with one or more of the compositions disclosed herein to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to diagnose or detect the disease.

In certain embodiments, kits are provided for determining the pH of a sample comprising:

(a) one or more of the pH-sensitive fluorescent dye compounds described herein;

(b) one or more containers; and optionally (c) instructions for determining the pH of the sample.

In certain embodiments, kits are provided for determining the pH of a sample comprising:

(a) one or more of the compositions described herein;

(b) one or more containers; and optionally (c) instructions for determining the pH of the sample.

In certain embodiments, processes are provided of synthesizing a compound of structural formula (I):

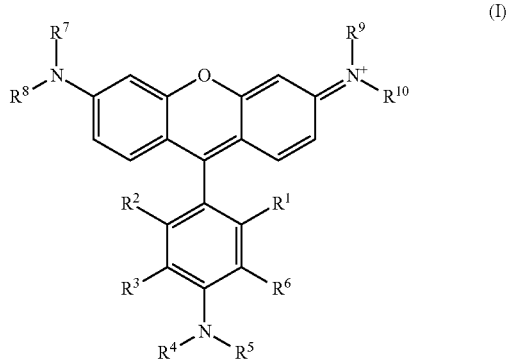

(I)

the process comprising:
contacting a compound of structural formula (III):

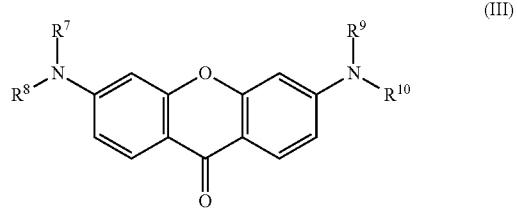

(III)

with a compound of structural formula (IV):

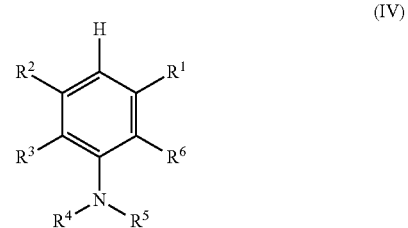

(IV)

to form a compound of structural formula (I), wherein $R^1$, $R^2$, $R^3$, $R^4$, $R^5$, $R^6$, $R^7$, $R^8$, $R^9$ and $R^{10}$ are as previously defined.

Other embodiments and illustrative aspects, features and advantages of the present invention will become apparent from the following detailed description. It should be understood, however, that the detailed description and the specific examples, while indicating preferred embodiments, are given by way of illustration only, since various changes and modifications within the spirit and scope of the present invention will become apparent to those skilled in the art from this detailed description.

BRIEF DESCRIPTION OF THE FIGURES

Although the following figures depict various examples of the invention, the invention is not limited to the examples depicted in the figures.

DETAILED DESCRIPTION

Figure 1:
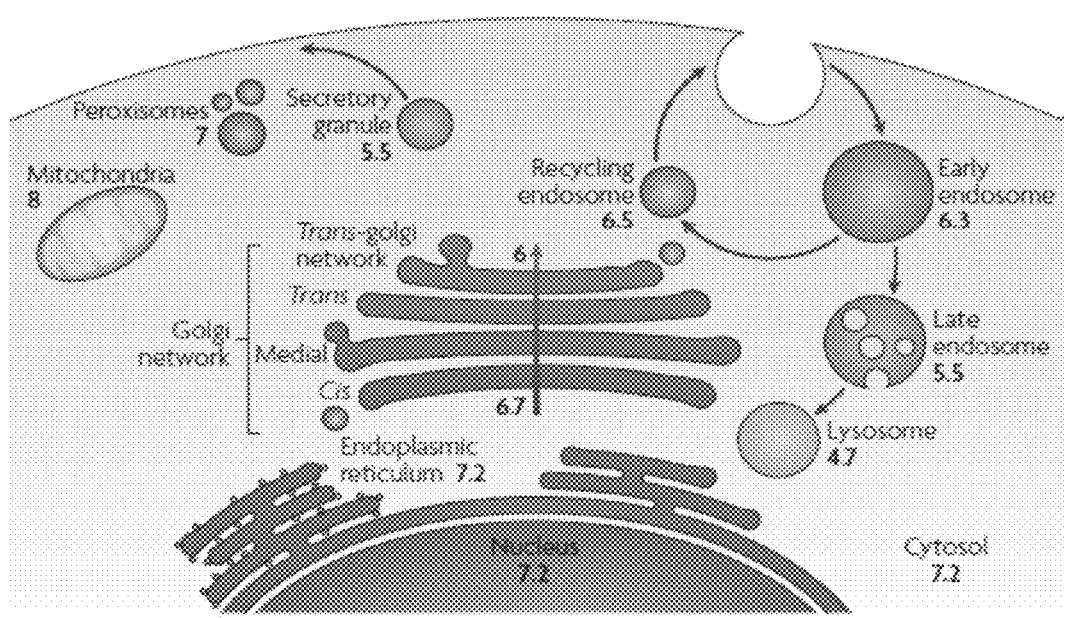
FIG. 1 is a schematic representation of the pH values for intracellular compartments and organelles.

A family of rhodamine-based pH sensors (Smith, et. al; PCT Publication No. WO 2005/098437, herein incorporated by reference in its entirety) displays pH-dependency based on the ionization state of the X substituent (see Scheme I below), namely a hydroxyl or thiol group, such that deprotonation of the —OH or —SH group to a negatively charged state quenches the fluorescence. It is only upon protonation of the negatively charged —O⁻ or —S⁻ that the fluorescence is restored as illustrated in Scheme 1:

air). In addition, strong electron withdrawing properties of the reporter tetramethylrhodamine moiety of the dyes described in Smith et al. significantly decrease the pKa of the indicator group at the X position of Scheme 1, thus shifting the sensors' working range towards acidic pH values.

In certain embodiments, therefore, the present invention provides pH-sensitive fluorescent dyes having an aniline moiety (of which the amino group may be substituted or modified as disclosed herein) wherein the benzene ring of the aniline moiety is free from hydroxy and thiol substituents ortho to the fluorophore or, in certain embodiments, free from hydroxy and thiol at all positions. In particular, these pH-sensitive fluorescent dye compounds may have, in place of the hydroxy or thiol substituent required by Smith et al. (supra), a moiety wherein the oxygen or sulfur of the hydroxy or thiol group has been incorporated into an ether or thioether linkage, for example as part of an alkoxy group or furan moiety, or their sulfur analogs. Viewed alterna-

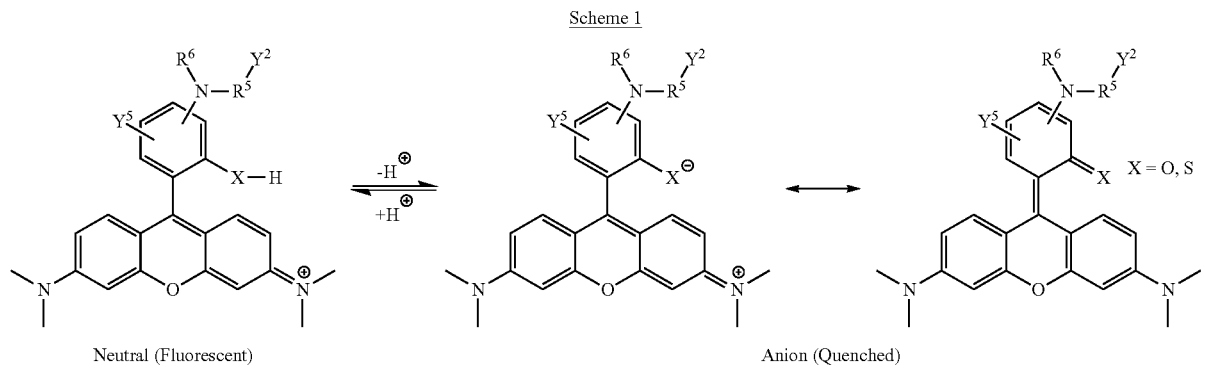

Scheme 1

Neutral (Fluorescent)    Anion (Quenched)    X = O, S

However, we have unexpectedly found that alkoxy substitutions at the corresponding X position are still capable of demonstrating a modulated fluorescence in response to a change in pH. Thus, while not wishing to be bound by a theory, we postulate that it is the protonation of the nitrogen at the 4 position on the aryl ring that modulates fluorescence. In any event, the present invention is predicated on the surprising discovery that the hitherto indispensable hydroxy or thiol group X may be dispensed with provided that a substituent nitrogen is retained. Advantageously, the addition of a dialkylamino group at the $R^3$ position resulted in a physiological pKa.

In addition, the pH-sensitive fluorescent dyes provided herein fluoresce in the red portion of the UV/VIS spectrum and have different chemical behavior as compared to other pH-sensitive dyes. It was surprisingly discovered that: 1) the electron withdrawing power of the aniline moiety may be modulated by adding various electron donating groups to the benzene ring, and 2) the addition of electron donating groups such as dialkylamino groups at the $R^3$ position and/or halogen at positions $R^2$ and/or $R^6$, may be used to tune the pKa of the pH-sensitive fluorescent dyes to be at or near physiological pH. Furthermore, by altering the electron donating groups at positions $R^1$-$R^6$, the pKa of the pH-sensitive fluorescent dye may be modulated to suit a particular need.

Further, we have found that the dyes described by Smith et al. (supra) are not stable in solution, most likely as a result of aerobic oxidation (e.g., oxidation by exposure to ambient tively, the pH-sensitive fluorescent dye compounds provided herein which retain the oxygen or sulfur in etherified form, are dye compounds which provide increased electronic density of the molecule through strategic introduction of electron donating groups (EDG) to the benzene ring resulting in an electron rich aniline moiety, thereby moving the pKa closer to a physiological range (e.g., pH 6-8). Accordingly, the benzene ring may be substituted one or more times (e.g., 1, 2, 3 or 4 times) by an electron donating group, the electron donating groups being the same or different. In certain embodiments, the pH-sensitive fluorescent dye compounds provided herein have the etherified O or S replaced by another electron donating group. Irrespective of whether the etherified O or S is replaced by another EDG, supplementary electron donating groups may be provided on the benzene ring to further modulate the pKa. In certain embodiments, the pH-sensitive fluorescent dye compounds provided herein may comprise two electron donating groups in total on the benzene ring, in particular two electron donating groups of the type having a lone pair of electrons available immediately next to the benzene ring (e.g. alkoxy or dialkylamino, optionally substituted as described herein). Additionally, modifications may be made to modulate the quantum yield of the pH-sensitive fluorescent dye compounds of the present disclosure. Thus, the pH-sensitive fluorescent dye compounds as disclosed herein have significant advantages over other PET-based dyes and advantageously provide the benefit of having improved stability and/or a pKa in the range of physiological applications. In addition, the pKa of the pH-sensitive fluorescent dye compounds provided herein may be tuned to particular pKa's depending on the electron donating group(s) used on the benzene ring (e.g., on the aniline moiety).

In certain embodiments, the pKa of the aniline's amino group is modulated by modifying the amino group into a more basic nitrogen functional group. This feature may usefully be adopted as an alternative to replacing the omitted hydroxy or thiol group with another electron donating group; alternatively, modification of the amino group into a more basic group may be combined with substitution of the benzene ring by at least one electron donating group other than a hydroxy or thiol group.

Also included herein are embodiments in which the pKa of the aniline moiety is modulated by modifying the amino group at position $R^3$ to —NR'R", wherein R' and R", which may be the same or different, are each independently alkyl or substituted alkyl (e.g., a dialkylamino group) in order to bring the pKa closer to the physiological range. In certain embodiments, the dialkylamino group is dimethylamino (e.g., —N(CH$_3$)$_2$). In certain embodiments, the dialkylamino group is diethylamino (e.g., —N(CH$_2$CH$_3$)$_2$).

Particular features targeted by the compounds, compositions, methods and kits described herein include one or more of: (1) dissociation constant pKa within the physiological range; (2) greater stability (considered to be towards oxidation); (3) flexible synthetic methods allowing introduction of pKa-modulating substituents along with reactive groups; and 4) tunability of the pKa. As described previously herein, the pH-sensitive fluorescent dye compounds of the present invention, have enhanced stability by dispensing with the previously indispensable hydroxy or thiol at position X of Scheme I, and the hydroxy or thiol group is advantageously replaced by another electron donating group at the same position, such as an alkoxy or thioalkyl, preferably an alkoxy. Additionally or alternatively, such other electron donating groups may be substituted at other positions on the benzene ring. In certain embodiments, such other electron donating groups include dialkylamino groups, wherein each alkyl group, which may be the same or different, is each independently alkyl or substituted alkyl.

In order to achieve these goals a novel class of the pH-sensitive compounds was designed, synthesized and tested in analytical and biological applications. The structures of the preferred dye compounds include structural formulae (I) and (II).

Substituents on an aromatic ring may either donate electrons to the aromatic ring or withdraw electrons from the aromatic ring as compared to a hydrogen atom attached to the ring. Substituents may therefore be classified as electron donating groups or electron withdrawing groups.

Many electron donating groups have lone pairs of electrons on the atom adjacent to the pi ($\pi$) system of the aromatic ring. Alkyl, aromatic and alkenyl groups are examples of electron donating groups. Electron withdrawing groups are generally those where the atom adjacent to the aromatic pi system has a formal positive charge or a $\delta$ positive charge (for example, due to being connected to more electronegative atoms). Electron donating groups have an activating effect with respect to further substitution of the ring system and tend to direct further substitution ortho/para, while electron withdrawing groups are deactivating and tend to direct further substitution meta. The exception to this is halogen substituents, which, while overall electron withdrawing and deactivating, tend to direct further substitution ortho/para due to resonance (lone pair) donation. Table 1 indicates the relative electron withdrawing and donating character of some common substituents.

TABLE 1

Relative electron donating/withdrawing character of different aromatic ring substituents, ranked from most electron donating to most electron withdrawing

| Substituent | Character relative to H | Activating/deactivating | Directing |
|---|---|---|---|
| —O$^-$ | electron donating | strongly activate | ortho/para |
| —NR$_2$ | electron donating | strongly activate | ortho/para |
| —NH$_2$ | electron donating | strongly activate | ortho/para |
| —OH | electron donating | strongly activate | ortho/para |
| —OR | electron donating | strongly activate | ortho/para |
| —NHC(O)R | electron donating | moderately activate | ortho/para |
| —OC(O)R | electron donating | moderately activate | ortho/para |
| —R | electron donating | weakly activate | ortho/para |
| —Ph | electron donating | weakly activate | ortho/para |
| —CH=CR$_2$ | electron donating | weakly activate | ortho/para |
| —H | reference | neutral | ortho/para |
| —X (X = halo) | electron withdrawing | weakly deactivate | ortho/para |
| —C(O)H | electron withdrawing | moderately deactivate | meta |
| —C(O)R | electron withdrawing | moderately deactivate | meta |
| —C(O)OR | electron withdrawing | moderately deactivate | meta |
| —C(O)OH | electron withdrawing | moderately deactivate | meta |
| —CF$_3$ | electron withdrawing | strongly deactivate | meta |
| —CN | electron withdrawing | strongly deactivate | meta |
| —S(O)$_2$OH | electron withdrawing | strongly deactivate | meta |
| —N$^{(+)}$H$_3$ | electron withdrawing | strongly deactivate | meta |
| —N$^{(+)}$R$_3$ | electron withdrawing | strongly deactivate | meta |
| —N$^{(+)}$(O)O$^{(-)}$ | electron withdrawing | strongly deactivate | meta |

The symbol R in Table 1 in particular stands for alkyl, though it may be substituted in any reasonable way which does not transform the electronic effect of alkyl from donating to withdrawing or vice-versa. This specification further describes suitable electron donating groups for phenylic substitution of the aniline or aniline-like ring described in the specification.

DEFINITIONS

To more clearly and concisely describe and point out the subject matter of the present teachings, the following definitions are provided for specific terms, which are used in the following description and appended claims. Throughout the specification, exemplification of specific terms should be considered as non-limiting examples.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a fluorescent pH sensitive dye" includes a plurality of dyes and reference to "a cell" includes a plurality of cells and the like. The phrase "and/or" denotes a shorthand way of indicating that the specific combination is contemplated in combination and separately, in the alternative. For illustration purposes, but not as a limitation, "X and/or Y" can mean "X" or "Y" or "X and Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The section headings used herein are for organizational purposes only and are not to be construed as limiting the desired subject matter in any way. All literature cited in the specification, including but not limited to, patents, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure is related. The following terms are defined for purposes of the teachings as described herein.

"Alkyl" refers to monovalent saturated aliphatic hydrocarbyl groups having from 1 to 10 carbon atoms and preferably 1 to 6 carbon atoms, e.g. 1, 2, 3, 4, 5 or 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxylalkyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein. Particular substituted alkyl groups comprise a reactive group for direct or indirect linking to a carrier molecule or solid support; as examples may be mentioned alkyl substituted by carboxyl or a carboxyl ester (e.g. an activated ester such as an N-hydroxysuccinimide ester) and alkyl substituted by aminocarbonyl —CONHR where R is an organic moiety as defined below with reference to the term "aminocarbonyl", e.g. a $C_1$-$C_{10}$ (e.g. $C_1$-$C_6$) alkyl terminally substituted by a reactive group ($R_x$) including, but not limited to, carboxyl, carboxylester, maleimide, succinimidyl ester (SE), sulfodichlorophenol (SDP) ester, sulfotetrafluorophenol (STP) ester, tetrafluorophenol (TFP) ester, acetoxymethoxy (AM) ester, nitrilotriacetic acid (NTA), aminodextran, and DIBO-amine.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl), wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O) substituted alkenyl, —NRC(O)alkynyl, —NRC(O) substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic, wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O) O—, aryl-C(O)O—, substituted aryl-C(O)O—, cycloalkyl- C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aniline" refers to C$_6$H$_5$NH$_2$, and consists of a phenyl ring attached to an amino group. As used herein, the amino group is para to a fluorophore, as is illustrated as follows:

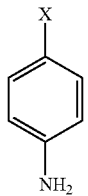

wherein X is a fluorophore, preferably a xanthene derivative, most preferably a rhodamine or rhodol.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl), where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, but-3-en-1-yl, and propenyl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Carboxyl" or "carboxy" refers to —COOH or salts thereof.

"Carboxyl alkyl" or "carboxyalkyl" refers to the groups —(CH$_2$)$_n$COOH, wherein n is an integer from 1 to 6.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic, wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclic, and substituted heterocyclic and two R$^{13}$ groups attached to a common guanidino nitrogen atom are optionally joined together with the nitrogen bound thereto to form a heterocyclic or substituted heterocyclic group, provided that at least one R$^{13}$ is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, and sulfonyl moieties.

"Substituted heterocyclic" or "substituted heterocycloalkyl" or "substituted heterocyclyl" refers to heterocyclyl groups that are substituted with from 1 to 5, or preferably 1 to 3 of the same substituents as defined for substituted cycloalkyl.

"Heterocyclyloxy" refers to the group —O-heterocyclyl.

"Substituted heterocyclyloxy" refers to the group —O-(substituted heterocyclyl).

"Heterocyclylthio" refers to the group —S— heterocyclyl.

"Substituted heterocyclylthio" refers to the group —S-(substituted heterocyclyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$— or =NNH—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^+$(alkyl)-NH$_2$.

"Nitro" refers to the group —NO$_2$.

"Oxo" refers to the atom (=O) or (—O$^-$).

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

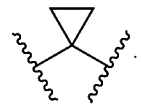 [SMILES: *C1(*)CC1]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl), wherein substituted alkyl is as defined herein.

A dashed line projecting from a substituent, such as:

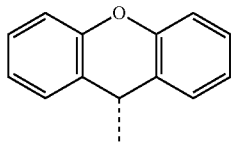

indicates the point of attachment to the base molecule. For a fused ring, dashed lines indicate portions of the base molecule where the fused ring is attached, such as:

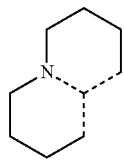

wherein the full molecule could have the structure:

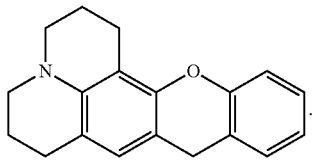 [SMILES: c1ccc2c(c1)Cc1cc3c4c(c1O2)CCCN4CCC3]

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

The pH-sensitive fluorescent dye compounds disclosed herein may exist in unsolvated forms as well as solvated forms, including hydrated forms. These compounds may exist in multiple crystalline or amorphous forms. In general, all physical forms are equivalent for the uses described herein and are intended to be within the scope of the present disclosure. The dye compounds disclosed herein may possess asymmetric carbon atoms (i.e., chiral centers) or double bonds; the racemates, diastereomers, geometric isomers and individual isomers of the compounds described herein are within the scope of the present disclosure. The dye compounds described herein may be prepared as a single isomer or as a mixture of isomers.

Where substituent groups are specified by their conventional chemical formulae and are written from left to right, they equally encompass the chemically identical substituents, which would result from writing the structure from right to left, e.g., —CH$_2$O— is intended to also recite —OCH$_2$—.

It will be understood that the chemical structures that are used to define the dye compounds disclosed herein are each representations of one of the possible resonance structures by which each given structure can be represented. Further, it will be understood that by definition, resonance structures are merely a graphical representation used by those of skill in the art to represent electron delocalization, and that the present disclosure is not limited in any way by showing one particular resonance structure for any given structure.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

The term "carrier molecule" as used herein, refers to a biological or a non-biological component that is or becomes covalently bonded to a pH-sensitive fluorescent dye compound disclosed herein. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. Included is one embodiment in which carrier molecules comprise an organic moiety having at least 4 plural valent atoms and often more than 10 plural valent atoms (i.e., atoms other than hydrogen and halo), e.g. at least 15 such atoms, as in the case of moieties having at least 20 such atoms.

The term "conjugated substance" or "$S_c$" refers to a carrier molecule or solid support.

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

The term "electron donating group" or "EDG" refers to a substituent with lone electron pairs that is adjacent to an aromatic ring, such as phenyl, and increases electron density on the ring through a resonance donating effect. Electron donating groups of the present disclosure include, for example, alkoxy, substituted alkoxy, amino, substituted amino, halogen, alkylthio, acylamino, and (carboxyl ester) oxy. Alkoxy is a particular EDG. Substituted alkoxy is another particular EDG. Also to be mentioned is dialkylamino. A further example is dialkylamino having a substituted alkyl group. Preferred EDGs are —OCH$_3$, —NH$_2$, —NHCH$_3$, —N(CH$_3$)$_2$, and —N(CH$_2$CH$_3$)$_2$, particularly —OCH$_3$, —NH$_2$, —NHCH$_3$, —N(CH$_3$)$_2$ and —N(CH$_2$CH$_3$)$_2$. Also to be mentioned are alkoxy, alkylthio and dialkylamino, in any of those instances having an alkyl substituent in which the alkyl part is substituted by a moiety or -L$_R$-S$_c$. The specification also discloses specific compounds or compound classes which include other EDGs than those with a lone pair of electrons adjacent an aromatic ring.

"Fluorescent pH-sensitive dye," "pH-sensitive fluorescent dye," and "fluorescent pH sensor dye" are equivalent and are used interchangeably to refer to a compound whose fluorescent spectrum or intensity is affected by pH.

The term "fluorophore" or "fluorogenic" as used herein refers to a composition that is inherently fluorescent or demonstrates a change in fluorescence upon protonation, or binding to a biological compound or metal ion, or metabolism by an enzyme. Preferred fluorophores of the present disclosure include fluorescent dyes having a high quantum yield in aqueous media. Exemplary fluorophores include xanthene derivatives, preferably rhodamines and rhodols. The fluorophores disclosed herein may be substituted to alter the solubility, spectral properties or physical properties of the fluorophore.

The term "linker" or "L", as used herein, refers to a single covalent bond or a moiety comprising series of stable covalent bonds, the moiety often incorporating 1-40 plural valent atoms selected from the group consisting of C, N, O, S and P that covalently attach the fluorogenic or fluorescent compounds to another moiety such as a chemically reactive group or a biological and non-biological component. The number of plural valent atoms in a linker may be, for example, 0, 1, 2, 3, 4, 5, 6, 7, 8, 9, 10, 20, 25, 30 or a larger number up to 40 or more. A linker may be linear or non-linear; some linkers have pendant side chains or pendant functional groups, or both. Examples of such pendant moieties are hydrophilicity modifiers, for example solubilizing groups like, e.g. sulfo (—$SO_3H$ or —$SO_3^-$). In certain embodiments, L is composed of any combination of single, double, triple or aromatic carboncarbon bonds, carbonnitrogen bonds, nitrogennitrogen bonds, carbonoxygen bonds and carbonsulfur bonds. Exemplary linking members include a moiety that includes C(O)NH—, —C(O)O—, —NH—, —S—, —O—, and the like. Linkers may, by way of example, consist of a combination of moieties selected from alkyl; C(O)NH—; —C(O)O—; —NH—; —S—; —O—; —C(O)—; —S(O)— where n is 0, 1 or 2; —O—; 5- or 6-membered monocyclic rings; and optional pendant functional groups, for example sulfo, hydroxy and carboxy. The moiety formed by a linker bonded to a reactive group ($R_x$) may be designated -L-$R_x$. The reactive group may be reacted with a substance reactive therewith, whereby the linker becomes bonded to a conjugated substance ($S_c$); in this case, the linker typically contains a residue of a reactive group (e.g. the carbonyl group of an ester) and may be designated "-$L_R$". A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleavable groups are known in the art. See, for example, Jung et al., *Biochem. Biophys. Acta*, 761:152-162 (1983); Joshi et al., *J. Biol. Chem.*, 265:14518-14525 (1990); Zarling et al., *J. Immunol.*, 124:913-920 (1980); Bouizar et al., *Eur. J. Biochem.*, 155:141-147 (1986); Park et al., *J. Biol. Chem.*, 261:205-210 (1986); Browning et al., *J. Immunol.*, 143:1859-1867 (1989). Moreover a broad range of cleavable, bifunctional (both homo- and hetero-bifunctional) spacer arms are commercially available.

An exemplary cleavable group, such as an ester, is a cleavable group that may be cleaved by a reagent, e.g., sodium hydroxide, resulting in a carboxylate-containing fragment and a hydroxyl-containing product.

The linker may be used to attach the pH-sensitive fluorescent dye compound to another component of a conjugate, such as a targeting moiety (e.g., antibody, ligand, non-covalent protein-binding group, etc.), an analyte, a biomolecule, a drug and the like.

In certain embodiments, -L- is of the formula -L1-(L2)$_p$-(L3)$_r$-, wherein p is 0 or 1; r is 0 or 1; L1 is a bond, —CONH—, —COO—, or a moiety comprising at least two amino acids; L2 is —(CH$_2$)—, —CH$_2$CH$_2$O—(CH$_2$CH$_2$O)$_s$—CH$_2$CH$_2$—, or alkylene having from 1 to 30 carbon atoms and unsubstituted or substituted by at least one R$^a$, e.g. 1, 2, 3, 4, 5 or 6 R$^a$; L3 is —CONH—(CH$_2$)$_t$—, —COO—(CH$_2$)$_t$— or a moiety comprising at least two amino acids, wherein: r is from 1 to 30, e.g., 1 to 20 as in the case of 1 to 10, such as 1, 2, 3, 4, 5 or 6; s is 0, 1, 2, 3, 4, 5, 6, 7, 8, 9 or 10, e.g., 1 to 7; t is from 1 to 30, e.g. 1 to 20 as in the case of 1 to 10, such as 1, 2, 3, 4, 5 or 6; R$^a$ is sulfo (—$SO_3H$ and/or —$SO_3^-$), hydroxy, carboxy or amino, particularly sulfo.

In certain embodiments, the total number of carbon atoms comprised in alkylene moieties in L is no more than 40, e.g., up to 35, 30, 25, 20, 15 or 10. In certain embodiments, there is only a single one of L1 and L3 which comprises a moiety comprising at least two amino acids.

In certain embodiments, p and r are both 0. In certain embodiments, p is 1 and r is 0. In another certain embodiments, p and r are both 1.

In certain embodiments, L1 is a bond, —CONH— or —COO—. In certain compounds L1 is a bond. In certain others, L1 is —CONH—.

In certain embodiments, L2 is —(CH$_2$)$_u$—, where u is from 1 to 10, e.g., 1, 2, 3, 4, 5 or 6. In certain embodiments, L2 is —CH$_2$CH$_2$O—(CH$_2$CH$_2$O)$_s$—CH$_2$CH$_2$— where s is from 1 to 7. In certain embodiments, L2 is alkylene having from 1 to 10 carbon atoms, e.g., 1, 2, 3, 4, 5 or 6 carbon atoms, and which is unsubstituted or substituted by 1, 2, 3, 4, 5 or 6 sulfo groups, e.g., 1 to 4 sulfo groups. For all L2 moieties mentioned in this paragraph, L1 is —CONH— in a particular class of compounds. For all L2 moieties mentioned in this paragraph and all -L1-L2- combinations mentioned in this paragraph, r is 0 in one class of compounds.

In certain embodiments, (r+t) is from 1 to 30, e.g., 1 to 20 as in the case of 1 to 10, such as 1, 2, 3, 4, 5 or 6, for example.

Exemplary linkers include, but are not limited to, the following: a single covalent bond (for example between alkyl and a carboxy group or ester of a carboxy group, or other reactive group); aminocarbonyl (for example linking an alkyl group to a conjugated lipophilic moiety); a PEG-NH—CO-moiety (for example linking an alkyl group to an NHS-ester or other reactive group); an alkylaminocarbonyl group (for example linking an alkyl group to an NHS-ester, amine or other reactive group); an alkylaminocarbonyl group having a pendant group comprising sulfo—e.g. a pendant sulfoalkyl group (for example linking an alkyl group to NHS-ester or other reactive group or to a lipophilic group); or a single covalent bond linking an alkyl group to a reactive group such as a carboxy group or ester thereof.

The terms "patient," "subject" or "individual" refer to mammals and includes humans and non-human mammals, such as monkeys, dogs, cats, pocket pets, horses, cows, pigs or rats.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "reactive group" (or "$R_x$"), as used herein, refers to a group that is capable of reacting with another chemical group to form a covalent bond, i.e., is covalently reactive under suitable reaction conditions, and generally represents a point of attachment for another substance. The reactive group is a moiety, such as carboxylic acid or succinimidyl ester, on the compounds of the present disclosure that is capable of chemically reacting with a functional group on a different compound to form a covalent linkage. Reactive groups generally include nucleophiles, electrophiles and photoactivatable groups.

Exemplary reactive groups include, but are not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides, succinimidyl esters (SE), sulfodichlorophenol (SDP) esters, sulfotetrafluorophenol (STP) esters, tetrafluorophenol (TFP) esters, acetoxymethoxy (AM) esters, nitrilotriacetic acids (NTA), aminodextrans, DIBO-amines and the like. Methods to prepare each of these functional groups are well known in the art and their application to or modification for a particular purpose is within the ability of one of skill in the art (see, for example, Sandler and Karo, eds., *Organic Functional Group Preparations*, Academic Press, San Diego, 1989).

The term "salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

The term "sample," as used herein, refers to any material that may contain an analyte of interest or cells. Typically, the sample is a live cell or a biological fluid that comprises endogenous host cells. Alternatively, the sample may be a buffer solution or an environmental sample for which pH determination is needed. The sample may be in an aqueous solution, a viable cell culture or immobilized on a solid or semi-solid surface such as a polyacrylamide gel, membrane blot or on a microarray.

The term "solid support," as used herein, refers to a matrix or medium that is substantially insoluble in liquid phases and capable of binding a molecule or particle of interest. Solid supports suitable for use herein include semi-solid supports and are not limited to a specific type of support. Useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose®, poly(acrylate), polystyrene, poly(acrylamide), polyol, agarose, agar, cellulose, dextran, starch, FICOLL®, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

The terms "stereoisomer" or "stereoisomers" refer to compounds that differ in the chirality of one or more stereocenters. Stereoisomers include enantiomers and diastereomers.

The term "tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The terms "treating" or "treatment" of a disease in a patient refer to 1) preventing the disease from occurring in a patient that is predisposed or does not yet display symptoms of the disease; 2) inhibiting the disease or arresting its development; or 3) ameliorating or causing regression of the disease.

Dye Compounds and Compositions:

In general, for ease of understanding the present disclosure, the pH-sensitive fluorescent dye compounds and corresponding substituents will first be described in detail, followed by various methods in which the pH-sensitive fluorescent dye compounds of the present disclosure are useful, which is followed by exemplary methods of use and synthesis of certain novel dye compounds that are particularly advantageous for use with the methods provided herein.

The pH-sensitive fluorescent dye compounds disclosed herein are useful for monitoring or detecting pH in a sample. For example, we have found that by introducing an electron donating group (EDG) into the 4-amino-2-hydroxyphenyl ring of a pH-sensitive fluorescent dye compound that we were able to tune the fluorescent properties of the pH-sensitive fluorescent dye compound (See, structural formulae I and II). In particular we were able to tune the pKa value and obtain a pH-sensitive dye compound with a pKa value compatible with live cell intracellular applications. We also found that replacing the hydroxyl at position $R^1$ with an alkoxy or thioalkyl moiety not only increased the stability of the dye compound in an aqueous environment but also resulted in a compound that was pH sensitive, an unexpected advantage in view of the teaching by Smith et al. (supra).

Advantageously, the addition of a dialkylamino group to the aniline moiety at position $R^3$ resulted in the unexpected advantage of yielding pKa values in the physiological range. In certain embodiments, the dialkylamino group is diethylamino. In certain embodiments, the dialkylamino group is dimethylamino.

In certain embodiments, the pKa value is about 6 to about 7. Without wishing to be bound by a theory, the pKa of the amino group of the aniline moiety of the compounds of structural formulae I and II appears to depend on the ability of the aromatic system to share a lone electron pair on the oxygen atom. This ability is affected by additional functional groups introduced into the aromatic system and thus, the pKa is tuned by adding EDG groups to pH sensitive dyes comprising an electron rich aniline moiety.

In certain embodiments, the sample to be analyzed includes live cells or a biological fluid, including cytosol that comprises endogenous host cell proteins, buffer solutions and environmental samples. Therefore, the pH-sensitive fluorescent dye compounds disclosed herein are useful for monitoring or determining pH changes and those events directly and indirectly associated with a change in pH. Monitoring of the pH may also be accomplished in live cells wherein the present pH-sensitive fluorescent dye compounds are internalized by live cells through a number of different mechanisms, including both passive and cell mediated mechanisms. For example, the present pH-sensitive fluorescent dye compounds may comprise a lipophilic group such as an acetoxymethoxy (AM) or acetate ester that allows for entry across the live cell membrane. Once inside the cells, nonspecific esterases cleave the AM or acetate ester resulting in a charged molecule that is well retained in the cell. Alternatively, the present pH-sensitive fluorescent dye compounds may be conjugated to a carrier molecule that allows the dye compound to be taken up by live cells. Examples include internalization during phagocytosis, wherein the pH-sensitive fluorescent dye compounds are conjugated to bacterial particles or other proteins (or peptides) that induce phagocytosis by macrophages or monocytes; or up-take through receptor internalization when the present pH-sensitive fluorescent dye compounds are conjugated to a carrier molecule that binds a receptor and thus induces internalization.

The pH-sensitive fluorescent dye compounds disclosed herein function as reporter molecules to confer a detectable signal, directly or indirectly, to the sample as a result of a change in pH. This results in the ability to measure and monitor pH changes in a sample to directly and indirectly detect specific events associated with a change in pH.

Where the detectable response is a fluorescence response, it is typically a change in fluorescence, such as a change in the intensity, excitation or emission wavelength, distribution of fluorescence, fluorescence lifetime, fluorescence polarization, or a combination thereof. In certain embodiments, the detectable optical response upon protonation is a change in fluorescence intensity that is greater than approximately 150% relative to the same dye compound wherein the aniline moiety is not protonated on the nitrogen. Preferably, the change in fluorescence intensity is greater than 5-fold, and more preferably more than 10-fold.

The pH-sensitive fluorescent dye compounds provided herein may comprise a fluorophore that may be any rhodamine or rhodol fluorophore known to one skilled in the art that fluoresces in the red portion of the UV/VIS spectrum. Preferably, the fluorophore is quenched, or substantially non-fluorescent, until the nitrogen on the aniline moiety is protonated.

In certain embodiments, the pH-sensitive fluorescent dye compounds are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group, solid support and carrier molecule. In another embodiment, the rhodamine and rhodol fluorophores disclosed herein comprise both substituted and unsubstituted moieties on the carbon atom of the central ring of the xanthene by substituents typically found in the xanthene-based dyes such as phenyl and substituted-phenyl moieties. Most preferred dyes are rhodamine, rhodol, and derivatives thereof. The choice of the fluorophore attached to the aniline moiety will determine the pH-sensitive compound's absorption and fluorescence emission properties as well as its live cell properties, i.e. ability to localize within a cell.

In certain embodiments, the fluorophore (e.g., rhodamine or rhodol) is attached to the aniline moiety via a linker. In certain embodiments, the fluorophore (and reactive group, carrier molecules, and solid support) comprise a linker that is used to covalently attach the substituents to the aniline moieties disclosed herein. The fluorophore (and solid support, carrier molecule or reactive group) may be directly attached to the moieties (where the linker is a single bond) or attached through a series of stable bonds. Preferably the fluorophore is directly attached by a single covalent bond to the aniline moiety, but may also be attached via a linker as described below for reactive group, carrier molecules, and solid support. When the linker is a series of stable covalent bonds the linker typically incorporates 1-30 nonhydrogen atoms selected from the group consisting of C, N, O, S and P. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that may be found in the linker ether, thioether, carboxamide, thiourea, sulfonamide, urea, urethane, hydrazine, alkyl, aryl, heteroaryl, alkoxy, cycloalkyl and amine moieties. Examples of a linker include, but are not limited to, substituted or unsubstituted polymethylene, arylene, alkylarylene, arylenealkyl, or arylthio.

In certain embodiments, the linker contains 1-6 carbon atoms. In certain embodiments, the linker comprises a thioether linkage. Exemplary linking members include a moiety that includes, but is not limited to, —C(O)NH—, —C(O)O—, —NH—, —S—, —O—, and the like. In certain embodiments, the linker is or incorporates the formula —(CH$_2$)$_d$(CONH(CH$_2$)$_e$)$_z$—, or where d is an integer from 0 to 5, e is an integer from 1 to 5 and z is 0 or 1. In certain embodiments, the linker is or incorporates the formula —O(CH$_2$)—. In certain embodiments, the linker is or incorporates a phenylene or a 2-carboxy-substituted phenylene.

Any combination of linkers may be used to attach the carrier molecule, solid support or reactive group and the present pH-sensitive fluorescent dye compounds together. The linker may also be substituted to alter the physical properties of the fluorophore or aniline moiety, such as spectral properties of the pH-sensitive fluorescent dye compounds.

Another important feature of the linker is to provide an adequate space between the carrier molecule, reactive group or solid support and the aniline moiety or fluorophore so as to prevent steric hindrance. Therefore, the linker of the pH-sensitive fluorescent dye compounds disclosed herein is important for (1) attaching the carrier molecule, reactive group or solid support to the dye compounds and attaching the fluorophore to the aniline moiety, (2) providing an adequate space between the carrier molecule, reactive group or solid support and the dye compound so as not to sterically hinder the action of the compound and (3) for altering the physical properties of the dye compounds disclosed herein.

The pH sensing or electron rich aniline moiety of the pH-sensitive fluorescent dye compounds disclosed herein is any moiety that, when protonated, results in the compound being fluorescent, whilst the dye compound is quenched when the aniline moiety is not in the protonated state. The pH-sensitive fluorescent dye compounds often have a pKa value in the range of about 2 to about 10. In certain embodiments the pKa of the pH-sensitive fluorescent dye compound is about 3 to about 10. In certain embodiments, the pKa of the pH-sensitive fluorescent dye compound is about 5 to about 8. In certain embodiments the pKa of the pH-sensitive fluorescent dye compound is about 6 to about 8. In certain embodiments the pKa of the pH-sensitive fluorescent dye compound is about 6 to about 7. In certain embodiment the pKa of the pH-sensitive fluorescent dye compound is about 6.5. Preferably the pKa of the pH-sensitive fluorescent dye compounds provided herein is about 6 to about 7.

To tune the pKa to about 6 to about 7, electron donating groups (EDG) were introduced into the aniline moiety on the aryl group. This combined with the presence of an alkoxy or other like substituents on the aryl when a OH or SH were not present, unexpectedly resulted in pH-sensitive fluorescent dye compounds that were stable in an aqueous environment and provided a pKa in the desired range. As disclosed in and with reference to the formulae herein, the amino group of the aniline moiety may be substituted or replaced by another basic moiety of higher pKa. Advantageously, the addition of a dialkylamino group, wherein each of the alkyl groups, which may be the same or different, is independently alkyl or substituted alkyl, to the aniline group at position $R^3$ resulted in the unexpected advantage of yielding pKa values in the physiological range. In certain embodiments, the dialkyl amino group is dimethylamino. In certain embodiments, the dialkylamino group is diethylamino.

In certain embodiments, without wishing to be bound by a theory, the functioning of the pH-sensitive fluorescent dye compounds provided herein as a pH indicator is illustrated below in Scheme 2:

Scheme 2

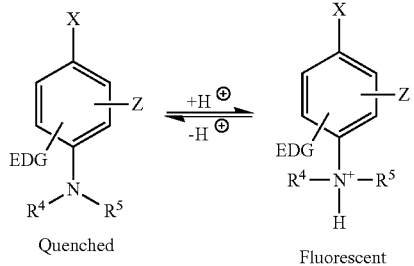

Quenched      Fluorescent wherein X is a fluorophore and $R^4$ and $R^5$ are as previously described herein.

The EDG is typically at $R^3$, but may be located at any position on the aryl group. Electron donating groups of the present invention include, for example, alkoxy, substituted alkoxy, amino, substituted amino, dialkylamino, halogen, alkylthio, acylamino, and (carboxyl ester)oxy. Preferred EDGs are —$OCH_3$, —$NH_2$, —$NHCH_3$, —$N(CH_3)_2$, —$N(CH_2CH_3)_2$, sulfotetraflurophenol (STP) ester, sulfordichlorophenol (SDP) ester, succinimidyl (SE) ester and tetrafluorophenol (TFP) ester. In certain embodiments, Z is O-alkyl. In certain embodiments, Z is thioalkyl.

In certain embodiments novel dye compounds are provided for use as fluorescent pH sensors, the dye compounds having structural formula (I):

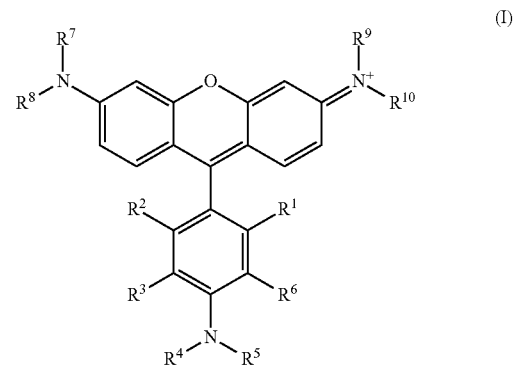

(I)

wherein $R^1$ is alkoxy or thioalkyl;

$R^2$ and $R^6$, which may be the same or different, are each independently H, halogen, —$OR^a$, —$SR^a$, —$NR^aR^b$, or an electron donating group;

$R^3$ is —NR'R", wherein R' and R", which may be the same or different, are each independently alkyl or substituted alkyl;

$R^4$ is selected from the group consisting of alkyl and substituted alkyl;

$R^5$ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$, wherein L is a linker, $R_x$ is a reactive group, and $S_c$ is a conjugated substance;

$R^a$ is H, alkyl, or substituted alkyl;

$R^b$ is alkyl or substituted alkyl; and $R^7$, $R^8$, $R^9$, and $R^{10}$, which may be the same or different, are each independently alkyl or alkenyl.

In certain embodiments, $R^1$-$R^{10}$ are as follows:

$R^1$ is alkoxy or thioalkyl;

$R^2$ and $R^6$, which may be the same or different, are each independently H or halogen;

R³ is —NR'R", wherein R' and R", which may be the same or different, are each independently alkyl;

R⁴ is alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and R⁷, R⁸, R⁹, and R¹⁰, which may be the same or different, are each independently alkyl or alkenyl.

In certain embodiments, R¹-R¹⁰ are as follows:
R¹ is alkoxy or thioalkyl;
R² and R⁶, which may be the same or different, are each independently H, Cl or F;
R³ is —NR'R", wherein R' and R", which may be the same or different, are each independently alkyl;
R⁴ is alkyl;
R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and R⁷, R⁸, R⁹, and R¹⁰, which may be the same or different, are each independently alkyl or alkenyl.

In certain embodiments, R¹-R¹⁰ are as follows:
R¹ is alkoxy or thioalkyl;
R² and R⁶ are each H;
R³ is —NR'R", wherein R' and R", which may be the same or different, are each independently alkyl;
R⁴ is alkyl;
R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and R⁷, R⁸, R⁹, and R¹⁰, which may be the same or different, are each independently alkyl or alkenyl.

In certain embodiments, R¹-R¹⁰ are as follows:
R¹ is methoxy; R² and R⁶ are each H;
R³ is —NR'R", wherein R' and R", which may be the same or different, are each independently methyl or ethyl;
R⁴ is methyl or ethyl;
R⁵ is methyl; ethyl; carboxyalkyl; $(CH_2)_nCO(O)R$; $(CH_2)_nC(O)R$; $(CH_2)_nC(O)NHR$; $(CH_2)_nC(O)NRR^c$; wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group selected from carboxyl, carboxylester, amide, maleimide, succinimidyl ester (SE), sulfodichlorophenol (SDP) ester, sulfotetrafluorophenol (STP) ester, tetrafluorophenol (TFP) ester, acetoxymethoxy (AM) ester, nitrilotriacetic acid (NTA), aminodextran, DIBO-amine; -L-$R_x$; or -L-$S_c$; and R⁷, R⁸, R⁹, and R¹⁰, which may be the same or different, are each independently methyl or propenyl.

In certain embodiments, novel dye compounds are provided for use as fluorescent pH sensors, the dye compounds having structural formula (II):

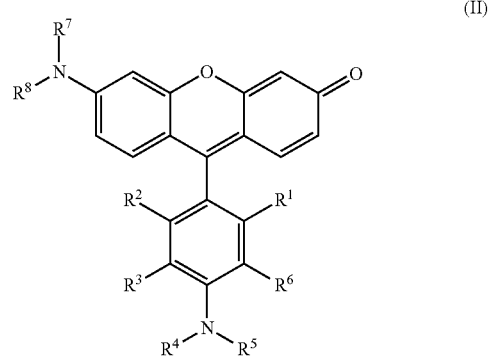

wherein
R¹ is alkoxy or thioalkyl;
R² and R⁶, which may be the same or different, are each independently H, halogen, —OR$^a$, —SR$^a$, —NR$^a$R$^b$, or an electron donating group;
R³ is —NR'R", wherein R' and R", which may be the same or different, are each independently alkyl or substituted alkyl;
R⁴ is selected from the group consisting of alkyl and substituted alkyl;
R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$, wherein L is a linker, $R_x$ is a reactive group, and $S_c$ is a conjugated substance;
R$^a$ is H, alkyl, or substituted alkyl;
R$^b$ is alkyl or substituted alkyl; and R⁷ and R⁸, which may be the same or different, are each independently alkyl or alkenyl.

In certain embodiments, R¹-R⁸ are as follows:
R¹ is alkoxy or thioalkyl;
R² and R⁶, which may be the same or different, are each independently H or halogen;
R³ is —NR'R", wherein R' and R", which may be the same or different, are each independently alkyl;
R⁴ is alkyl;
R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and
R⁷ and R⁸, which may be the same or different, are each independently alkyl or alkenyl.

In certain embodiments, R¹-R⁸ are as follows:
R¹ is alkoxy or thioalkyl;
R² and R⁶, which may be the same or different, are each independently H, Cl or F;
R³ is —NR'R", wherein R' and R", which may be the same or different, are each independently alkyl;
R⁴ is alkyl;
R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and
R⁷ and R⁸, which may be the same or different, are each independently alkyl or alkenyl.

In certain embodiments, R¹-R⁸ are as follows:
R¹ is alkoxy or thioalkyl;
R² and R⁶ are each H;
R³ is —NR'R", wherein R' and R", which may be the same or different, are each independently alkyl;
R⁴ is alkyl;
R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC$(O)NHR_x, wherein n is an integer from 1 to 6, and $R_x$ is a reactive group; -L-$R_x$; and -L-$S_c$; and
R⁷ and R⁸, which may be the same or different, are each independently alkyl or alkenyl.

In certain embodiments, R¹-R⁸ are as follows:
R¹ is methoxy;
R² and R⁶ are each H;
R³ is —NR'R", wherein R' and R", which may be the same or different, are each independently methyl or ethyl;
R⁴ is methyl or ethyl;
R⁵ is methyl; ethyl; carboxyalkyl; $(CH_2)_nCO(O)R$; $(CH_2)_nC(O)R$; $(CH_2)_nC(O)NHR$; $(CH_2)_nC(O)NRR^c$; wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group selected from carboxyl, carboxylester, amide, maleimide, succinimidyl ester (SE), sulfodichlorophenol (SDP) ester, sulfotetrafluorophenol (STP) ester, tetrafluorophenol (TFP) ester, acetoxymethoxy (AM) ester, nitrilotriacetic acid (NTA), aminodextran, DIBO-amine; -L-$R_x$; or -L-$S_c$;
R⁷ and R⁸, which may be the same or different, are each independently methyl or propenyl.

In certain embodiments, the EDG is selected from the group consisting of alkoxy, substituted alkoxy, amino, substituted amino, halogen, alkylthio, acylamino, and (carboxyl ester)oxy. In certain embodiments, the EDG is not hydroxy or thiol. In certain embodiments, the EDG is a dialkylamino group. In certain embodiments, the dialkylamino group is dimethylamino or diethylamino.

In certain embodiments, R¹ is —OCH₃ and R³ is —N(CH₃)₂ or —N(CH₂CH₃)₂.

In certain embodiments, R⁴ and R⁵ are alkyl or substituted alkyl. In certain embodiments, R⁵ is methyl; ethyl; carboxyalkyl; $(CH_2)_nCO(O)R$; $(CH_2)_nC(O)R$; $(CH_2)_nC(O)NHR$; $(CH_2)_nC(O)NRR^c$; wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group selected from carboxyl, carboxylester, amide, maleimide, succinimidyl ester (SE), sulfodichlorophenol (SDP) ester, sulfotetrafluorophenol (STP) ester, tetrafluorophenol (TFP) ester, acetoxymethoxy (AM) ester, nitrilotriacetic acid (NTA), aminodextran, DIBO-amine; -L-$R_x$; or -L-$S_c$.

In certain embodiments of any of the previous embodiments, the pKa of the pH-sensitive fluorescent dye compound is about 5 to about 8. In certain embodiments, the pKa of the pH-sensitive fluorescent dye compound is about 6 to about 8. In certain embodiments, the pKa of the pH-sensitive fluorescent dye compound is about 6 to about 7. In certain embodiments, the pKa of the pH-sensitive fluorescent dye compound is about 6.5. In certain embodiments, the pKa of the pH-sensitive fluorescent dye compound is about 3 to about 10.

The 4-position nitrogen of the aniline or aniline-like ring of the compounds disclosed herein does of course always have a permissible valency.

Reactive Groups:

In certain embodiments, the pH-sensitive fluorescent dye compounds provided herein are chemically reactive, and are substituted by at least one reactive group ($R_x$). The reactive group functions as the site of attachment for another moiety, such as a carrier molecule or a solid support, wherein the reactive group chemically reacts with an appropriate reactive or functional group on the carrier molecule or solid support. Thus, in certain embodiments, the pH-sensitive fluorescent dye compounds provided herein comprise an aniline moiety, linker, fluorophore, a reactive group moiety and optionally a carrier molecule and/or a solid support.

In certain embodiments, the pH-sensitive fluorescent dye compounds provided herein further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In certain embodiments, at least one member selected from $R^1$, $R^2$, $R^3$, $R^4$, $R^5$, and $R^6$ is a reactive group. Preferably, at least one of $R^3$, $R^4$, $R^5$, and $R^6$ is a reactive group, most preferred is at least one of $R^4$ or $R^5$. Alternatively, if the pH-sensitive fluorescent dye compounds disclosed herein comprise a carrier molecule or solid support a reactive group may be covalently attached independently to those substituents, allowing for further conjugation to a fluorophore, carrier molecule or solid support.

These reactive groups are synthesized during the formation of the pH-sensitive fluorescent dye compounds provided herein and carrier molecule- and/or solid support-containing compounds to provide chemically reactive pH-sensitive fluorescent dye compounds. In this way, pH-sensitive fluorescent dye compounds incorporating a reactive group may be covalently attached to a wide variety of carrier molecules or solid supports that contain, or are modified to contain, functional groups with suitable reactivity, resulting in chemical attachment of the components. In certain embodiments, the reactive group of the pH-sensitive fluorescent dye compounds disclosed herein and the functional group of the carrier molecule or solid support comprise electrophiles and nucleophiles that can generate a covalent linkage between them. In certain embodiments, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the pH-sensitive fluorescent dye compounds disclosed herein to the carrier molecule or solid support. Selected examples of functional groups and linkages are shown in Table 2, where the reaction of an electrophilic group and a nucleophilic group yields a covalent linkage.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |

TABLE 2-continued

Examples of some routes to useful covalent linkages

| Electrophilic Group | Nucleophilic Group | Resulting Covalent Linkage |
|---|---|---|
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a suitable leaving group (e.g., succinimidyloxy (—OC$_4$H$_4$O$_2$) sulfosuccinimldyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^x$ or —NR$^x$NHR$^y$, where R$^x$ and R$^y$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates.

The choice of the reactive group used to attach the pH-sensitive fluorescent dye compounds disclosed herein to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica.

Preferably, reactive groups react with an amine or a thiol functional group, or with silica. In certain embodiments, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. As used herein, "reactive platinum complex" refers to chemically reactive platinum complexes such as described in U.S. Pat. No. 5,714,327, herein incorporated by reference in its entirety.

In certain embodiments, the pH-sensitive fluorescent dye compounds disclosed herein comprise at least one reactive group that selectively reacts with an amine group. This amine-reactive group is selected from the group consisting of succinimidyl ester (SE), sulfonyl halide, tetrafluorophenyl (TFP) ester, sulfodichlorophenol (SDP) ester, sulfotetrafluorophenol (STP) ester, acetoxymethoxy (AM) ester, nitrilotriacetic acid (NTA), aminodextran, DIBO-amine and iosothiocyanates. Thus, in certain embodiments, the pH-sensitive fluorescent dye compounds provided herein form a covalent bond with an amine containing molecule in a sample. In certain embodiments, the pH-sensitive fluorescent dye compounds provided herein comprise at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904, all of which are herein incorporated by reference in their entirety).

Where the reactive group is an activated ester of a carboxylic acid, such as a succinimidyl ester of a carboxylic acid, a sulfonyl halide, a tetrafluorophenyl (TFP) ester, a sulfodichlorophenol (SDP) ester, a sulfotetrafluorophenol (STP) ester, an acetoxymethoxy (AM) ester, a nitrilotriacetic acid (NTA), an aminodextran, a DIBO-amine or an isothiocyanate, the resulting pH-sensitive fluorescent dye compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904, all of which are herein incorporated by reference in their entirety) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a certain embodiments, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In certain embodiments, the reactive group is a succinimidyl ester of a carboxylic acid, a sulfonyl halide, a tetrafluorophenyl ester, an iosothiocyanates or a maleimide. In certain embodiments, the reactive group is selected from sulfodichlorophenyl (SDP) ester, sulfotetrafluorophenol (STP) ester, succinimidyl (SE) ester and tetrafluorophenol (TFP) ester.

Carrier Molecules:

In certain embodiments, the pH-sensitive fluorescent dye compounds provided herein are covalently bound to a carrier molecule. If the pH-sensitive fluorescent dye compound has a reactive group, then the carrier molecule can alternatively be linked to the pH-sensitive fluorescent dye compound through the reactive group. The reactive group may contain both a reactive functional moiety and a linker, or only the reactive functional moiety.

A variety of carrier molecules are useful herein. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, polymers and bacterial particles. In certain embodiments, at least one member selected from $R^1$, $R^2$, $R^3$, $R^4$, $R^5$, and $R^6$ is a carrier molecule. Preferably, at least one of $R^3$, $R^4$, $R^5$, and $R^6$ is a carrier molecule, most preferred is at least one of $R^4$ or $R^5$.

In certain embodiments, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In certain embodiments, the carrier molecule is selected from a hapten, a nucleotide, an oligonucleotide, a nucleic acid polymer, a protein, a peptide or a polysaccharide. In certain embodiments the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In certain embodiments, the carrier molecule is an antibody or fragment thereof, an antigen, an avidin or streptavidin, a biotin, a dextran, an IgG binding protein, a fluorescent protein, agarose, and a non-biological microparticle. In certain embodiments, carrier molecules may comprise a label or a fluorescent dye or quencher.

In certain embodiments, the carrier molecule is an amino acid (including those that are protected or are substituted by phosphates, carbohydrates, or $C_1$ to $C_{22}$ carboxylic acids), or a polymer of amino acids such as a peptide or protein. In certain embodiments, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, a growth factor, bacterial particle or a binding partner for a cell receptor.

In certain embodiments, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In certain embodiments, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In certain embodiments, the carrier molecule comprises a carbohydrate or polyol that is typically a polysaccharide, such as dextran, FICOLL®, heparin, glycogen, amylopectin, mannan, inulin, starch, agarose and cellulose, or is a polymer such as a poly(ethylene glycol). In certain embodiments, the polysaccharide carrier molecule includes dextran, agarose or FICOLL®.

In certain embodiments, the carrier molecule comprises a lipid (typically having 6-25 carbons), including glycolipids, phospholipids, and sphingolipids. In certain embodiments, the carrier molecule comprises a lipid vesicle, such as a liposome, or is a lipoprotein. Some lipophilic substituents are useful for facilitating transport of the conjugated dye into cells or cellular organelles.

In certain embodiments, the carrier molecule is a cell, cellular system, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In certain embodiments, embodiment, the carrier molecule non-covalently associates with organic or inorganic materials. Exemplary embodiments of the carrier molecule that possess a lipophilic substituent may be used to target lipid assemblies such as biological membranes or liposomes by non-covalent incorporation of the pH-sensitive fluorescent dye compound within the membrane, e.g., for use as probes for membrane structure or for incorporation in liposomes, lipoproteins, films, plastics, lipophilic microspheres or similar materials.

In certain embodiments, the carrier molecule comprises a specific binding pair member wherein the pH-sensitive fluorescent dye compounds provided herein are conjugated to a specific binding pair member and used to the formation of the bound pair. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds disclosed herein function as a reporter molecule for the specific binding pair. Exemplary binding pairs are set forth in Table 3.

TABLE 3

Representative Specific Binding Pairs

| Antigen | Antibody |
| --- | --- |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization Solid Supports:

In certain embodiments, the pH-sensitive dye compounds disclosed herein are covalently bonded to a solid support. The solid support may be attached to the dye compounds either through the aniline moiety, fluorophore, or through a reactive group, if present, or through a carrier molecule, if present. Even if a reactive group and/or a carrier molecule are present, the solid support may be attached through the aniline moiety or fluorophore. In certain embodiments, at least one member selected from $R^1$, $R^2$, $R^3$, $R^4$, $R^5$, and $R^6$ is a solid support. Preferably, at least one of $R^3$, $R^4$, $R^5$, and $R^6$ is a solid support, most preferred is at least one of $R^4$ or $R^5$.

Solid supports suitable for use herein are typically substantially insoluble in liquid phases. Solid supports for use herein are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose®, poly(acrylate), polystyrene, poly(acrylamide), polyol, agarose, agar, cellulose, dextran, starch, FICOLL®, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In certain embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the dye compounds disclosed herein. Useful reactive groups are disclosed above and are equally applicable to the solid support reactive functional groups herein.

A suitable solid phase support may be selected on the basis of desired end use and suitability for various synthetic protocols. For example, where amide bond formation is desirable to attach the pH-sensitive fluorescent dye compounds disclosed herein to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Preparation of Conjugates:

In certain embodiments, conjugates of the pH-sensitive fluorescent dye compounds disclosed herein are provided. Conjugates of components (carrier molecules or solid supports), e.g., drugs, peptides, toxins, nucleotides, phospholipids, proteins and other organic molecules are prepared by organic synthesis methods using the pH-sensitive fluorescent dye compounds disclosed herein, are generally prepared by means well recognized in the art (Haugland, MOLECULAR PROBES HANDBOOK, supra, (2002)). Preferably, conjugation to form a covalent bond consists of mixing the reactive dye compounds disclosed herein in a suitable solvent in which both the pH-sensitive fluorescent dye compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of peptide or protein conjugates typically comprises first dissolving the protein to be conjugated in aqueous buffer at about 1-10 mg/mL at room temperature or below. Bicarbonate buffers (pH about 8.3) are especially suitable for reaction with succinimidyl esters, phosphate buffers (pH about 7.2 to about 8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the compound are added to the protein, the conjugate is chromatographically purified to separate unconjugated compound and the compound-protein conjugate is tested in its desired application.

Following addition of the pH-sensitive fluorescent dye compound to the component solution, the mixture is incubated for a suitable period (typically about 1 hour at room temperature to several hours on ice), the excess pH-sensitive fluorescent dye compound is removed by gel filtration, dialysis, HPLC, adsorption on an ion exchange or hydrophobic polymer or other suitable means. The pH-sensitive fluorescent dye compound-conjugate may be used in solution or lyophilized. In this way, suitable conjugates may be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3:2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye compound. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the pH-sensitive fluorescent dye compounds disclosed herein, an excess of pH-sensitive fluorescent dye compound is typically used, relative to the expected degree of pH-sensitive fluorescent dye compound substitution. Any residual, unreacted pH-sensitive fluorescent dye compound or a pH-sensitive fluorescent dye compound hydrolysis product is typically removed by dialysis, chromatography or precipitation. Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In certain embodiments, the conjugates disclosed herein are associated with an additional substance, that binds either to the fluorophore or the conjugated substance (carrier molecule or solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

In certain embodiments, compositions are provided for determining the pH of a sample, the compositions comprising:

a) one or more of the pH-sensitive fluorescent dye compounds described herein; and b) a carrier, wherein the one or more of the pH-sensitive fluorescent dye compounds are present in an amount effective to detect the pH of the sample.

In certain embodiments, compositions are provided for determining the pH of a sample, the compositions comprising:

(a) one or more of the pH-sensitive fluorescent dye compounds described herein; and (b) an analyte, wherein the one or more of the pH-sensitive fluorescent dye compounds are present in an amount effective to detect the pH of the sample.

In certain embodiments, the analyte is a cell and the pH-sensitive fluorescent dye compound is located inside the cell. In certain embodiments, the analyte is a protein, lipid or nucleic acid. In certain embodiments, the pH-sensitive fluorescent dye compound is conjugated to a carrier molecule.

Methods:

In certain embodiments, the pH-sensitive fluorescent dye compounds, dye-conjugates and compositions provided herein may be used in methods including, but not limited to, methods to determine the pH of living cells or cell compartments, to determine a change in pH to the local environment caused by a cell, and directly and indirectly detect specific cellular events associated with a change in pH. In certain embodiments, the methods involve detecting contamination in cell culture or on agar plates. For sake of clarity, the sample may also include material other than live cells and cell compartments such as, but not limited to, cell culture medium, biological fluids, diagnostic materials, and bacterial medium such as agar plates. As used herein, the term "a cell compartment" refers to one of the many organelles suspended in the cell cytoplasm. The pH of a cell or cell compartment may be measured by introducing one or more of the pH-sensitive fluorescent dye compounds, dye conjugates or compositions provided herein into a cell or cell compartment, irradiating the dye or dye conjugate with a suitable light source, and observing the intensity of fluorescence of the dye or conjugate. The observed fluorescence intensity may then be used to determine pH by a variety of methods known in the field, selected according to the method of accumulation of the dye or dye conjugate. For instance, the observed fluorescence may be compared to a known standard, for example a calibration curve of fluorescence intensity versus pH, or to fluorescence intensity measurements indicative of the total pH-sensitive fluorescent dye compound, dye conjugate, or composition present. Any conventional fluorimetric equipment may be used to irradiate the sample, and to measure the resulting fluorescent response.

As stated above, the sample may comprise live cells, intracellular fluids, extracellular fluids, biological fluids, sera, biological fermentation media, environmental sample, industrial samples, proteins, peptides, buffer solutions, biological fluids or chemical reactors, blood cells, immune cells, cultured cells, muscle tissue, neurons, extracellular vesicles; vascular tissue, blood fluids, saliva, urine, water, soil, waste water, sea water; pharmaceuticals, foodstuffs or beverages. In certain embodiments, the sample is immobilized on a polymeric membrane, within a polymeric gel, on a microparticle, on a microarray, on a silicon chip, on a glass slide, on a microwell plate, and on a microfluidic chip.

The pH-sensitive fluorescent dye compounds disclosed herein may therefore be used as pH sensors in relation to samples comprising or suspected of comprising a biological entity or biological substance. The pH-sensitive fluorescent dye compounds disclosed herein may be used in assays involving a biological entity or biological substance. In certain embodiments, the current teachings provide for the use of the pH-sensitive fluorescent dye compounds in a biological assay for the purposes described herein, particularly as a pH sensor.

Thus, in certain embodiments, the methods disclosed herein comprise determining the pH of a sample, wherein the methods comprise:

(a) contacting the sample with one or more of the pH-sensitive fluorescent dye compounds disclosed herein, to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to determine the pH of the sample.

In certain embodiments, the methods disclosed herein comprise determining the pH of a sample, wherein the methods comprise:

(a) contacting the sample with one or more of the compositions provided herein to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to determine the pH of the sample.

In certain embodiments, the pH-sensitive fluorescent dye compounds disclosed herein are used in cell culture for detection of contamination. In certain embodiments, the pH-sensitive fluorescent dye compounds disclosed herein are used in or on agar plates for the detection of contamination.

In certain embodiments, a change in the pH inside the cell corresponds to a cellular process. In certain embodiments, the pH-sensitive fluorescent dye compound is conjugated to a protein, nucleic acid or lipid. In certain embodiments, the pH-sensitive fluorescent dye compound is conjugated to transferrin. In certain embodiments, the pH-sensitive fluorescent dye compound is conjugated to a carrier molecule through a succinimidyl ester. In certain embodiments the pH-sensitive fluorescent dye compound is conjugated to epithelial growth factor (EGF) or EGF receptor (EGFR). In certain embodiments the pH-sensitive fluorescent dye compound is non-fluorescent before entering the cell. More particularly, the pH-sensitive fluorescent dye compound becomes fluorescent after entering the cell. In certain embodiments, the pH-sensitive fluorescent dye compound enters the cell through phagocytosis. In certain embodiments, the pH-sensitive fluorescent dye compound enters the cell through receptor-mediated endocytosis.

In certain embodiments, methods are provided for monitoring the pH inside a live cell, the methods comprising:

(a) contacting the cell with one or more of the pH-sensitive fluorescent dye compound disclosed herein to form a contacted cell;

(b) incubating the contacted cell for a sufficient amount of time for the one or more pH-sensitive fluorescent dye compounds to enter the cell to form a labeled cell;

(c) illuminating the labeled cell with an appropriate wavelength to form an illuminated cell; and (d) detecting fluorescent emissions from the illuminated cell;

wherein the fluorescent emissions are used to monitor the pH inside the cell.

In certain embodiments, methods are provided for monitoring the pH inside a live cell, the methods comprising:

(a) contacting the cell with one or more of the compositions provided herein to form a contacted cell;

(b) incubating the contacted cell for a sufficient amount of time for the one or more compositions to enter the cell to form a labeled cell;

(c) illuminating the labeled cell with an appropriate wavelength to form an illuminated cell; and (d) detecting fluorescent emissions from the illuminated cell;

wherein the fluorescent emissions are used to monitor the pH inside the cell.

Typically, the pH-sensitive fluorescent dyes and/or dye conjugates and/or compositions disclosed herein are introduced into a living cell or cell compartment by mixing with a sample comprising a cell or cell compartment, and then leaving the mixture to incubate for a time interval adequate to allow entry of the pH-sensitive fluorescent dye, dye conjugate, or composition into the cell or cell compartment. During this time interval, the pH-sensitive fluorescent dye compound, dye conjugate, or composition either passively diffuses across the plasma membrane or is taken up by the cell or cell compartment by a cell mediated mechanism.

In the case of conjugates, typically target molecules, including bacterial particles that induce phagocytosis and specific binding patterns that bind a cellular receptor and induce receptor internalization, are generally cell or cell compartment specific, hence a specific conjugate generally attaches to only one kind of cell or cell compartment. Once attached to a cell or cell compartment, the pH-sensitive fluorescent dye conjugate may diffuse through a membrane of that cell or cell compartment or be trafficked to a specific cell compartment by receptor-mediated endocytosis, hence exposing itself to the internal pH of the cell or cell compartment.

Advantageously, the pH-sensitive fluorescent dye compounds, dye conjugates, and compositions disclosed herein allow for a more accurate determination of pH as compared to existing pH sensor dyes because the pKa's of the pH-sensitive fluorescent dye compounds, dye conjugates, and compositions disclosed herein may, by design, be adjusted by substitution to a variety of pKa values. This is accomplished by the addition of EDG groups on the aniline moiety and by substitution at one of the remaining $R^1$-$R^6$ with a group that is not OH or SH. Thus, some are tuned to the pH of the cell or cell compartment of interest, and consequently will be ideal for measuring the pH of a cell or cell compartment when accumulated by receptor-mediated endocytosis or any non-passive accumulation mechanism as well as by passive accumulation. Others will have a pKa far from the pH of the cell media or extracellular matrix. The pH-sensitive fluorescent dye compounds disclosed herein are tuned to match the sample of choice with the understanding that the compounds become fluorescent when the pH of the sample drops below the pKa of the pH-sensitive fluorescent dye compound(s) disclosed herein. In certain embodiments, the pKa of the pH-sensitive fluorescent dye compound may be modified by the addition of a dialkyl amino group at position $R^3$ advantageously resulting in a physiological pKa. In certain embodiments, the dialkyl amino group is diethylamino. In certain embodiments, the dialkylamino group is dimethylamino.

Accumulation will occur passively when one form of the pH-sensitive fluorescent dye compound, dye conjugate, or composition with respect to pH (the uncharged form) freely penetrates the cell or cell compartment of interest and the other form (a charged form) is non-penetrating. Fluorescence will approach its equilibrium position provided the form of the accumulated dye is the fluorescent form and that accumulation to equilibrium has occurred. The observed fluorescence intensity may then be used to determine pH according to any of the known methods, for instance by reference to calibration data, or by comparing the observed fluorescence intensity to the fluorescence intensity observed on acidifying the test sample so that all the dye or conjugate fluoresces, the ratio of the two fluorescence intensities coupled with the known pKa allowing determination of pH. Passive accumulation may be achieved by use of a pH-sensitive fluorescent dye compound that is not attached to a carrier molecule or solid support or a pH-sensitive fluorescent dye compound that is attached to a small, relatively hydrophobic target molecule capable of diffusing through the cell membrane, such as one or more acetoxymethoxy (AM) ester groups. However, we have found that pH-sensitive fluorescent dye compounds comprising a reactive group, such as succinimidyl ester, also appear to passively accumulate in cells.

In certain embodiments, methods are provided for identifying a target cell within a population of cells wherein the target cell is differentially labeled relative to neighboring cells within the population, the methods comprising:

(a) contacting one or more of the pH-sensitive fluorescent dye compounds disclosed herein with the population of cells to form a contacted cell population;

(b) incubating the contacted cell population for a period of time sufficient for the one or more pH-sensitive fluorescent dye compounds to enter the target cell, thereby forming an incubated cell population; and (c) illuminating the incubated cell population, wherein the target cell is identified by a differential label relative to neighboring cells within the population.

In certain embodiments, methods are provided for identifying a target cell within a population of cells wherein the target cell is differentially labeled relative to neighboring cells within the population, the methods comprising:

(a) contacting one or more of the compositions disclosed herein with the population of cells to form a contacted cell population;

(b) incubating the contacted cell population for a period of time sufficient for the one or more composition to enter the target cell, thereby forming an incubated cell population; and (c) illuminating the incubated cell population, wherein the target cell is identified by a differential label relative to neighboring cells within the population.

In certain embodiments, the target cell is a neuronal cell. In certain embodiments, the neuronal cell is identified by increased fluorescence as compared with neighboring cells. In certain embodiments, the population of cells is part of a tissue. More particularly, the tissue is selected from the group consisting of tumor tissue, epidermal tissue, muscle tissue, bone marrow tissue, neural tissue, brain tissue, organ tissue, and human biopsy tissue.

In certain embodiments, methods are provided for identifying a first neuron or plurality of neurons in a neural tissue slice, or a neuronal cell is a heterogeneous mixture comprising neuronal and non-neuronal cell types. Also provided are methods for detecting the effect of a neuromodulator on a connection between neurons or a plurality of neurons forming a circuit; methods for identifying an inhibitory connection between or on neurons; and methods for identifying neurons in vivo or in vitro.

In certain embodiments, healthy neurons are identified in mixed cultures of living cells or preparations of cells, such as tissue slices or whole mount. In vivo identification of neurons or other metabolically active cells such as cardiac and skeletal myocytes are particularly preferred methods employing the pH-sensitive dye compounds disclosed herein.

Non-passive accumulation may occur through cell-mediated mechanism such as phagocytosis and endocytosis, typically when a pH-sensitive fluorescent dye compound disclosed herein comprises a carrier molecule or solid support that is bound by a cellular receptor. In this instance, whenever the dye compound provided herein is accumulated in the cell or cell compartment by a mechanism that does not rely solely on passive accumulation, the accuracy of a pH measurement will be highest when the pKa of the dye compound is near the pH to be measured. In this situation, without wishing to be bound by a theory, the increased accuracy available with the pH-sensitive dye compounds disclosed herein may arise from the fact that the pKa is the pH of the aqueous medium containing a species when it is 50% protonated and that at this pH a change in proton intensity will have greatest effect on the properties of the species. Hence, the greatest change in fluorescence intensity occurs at the pKa of the pH-sensitive fluorescent dye, and measurements of absolute fluorescence intensity at this pH so that the pH-sensitive fluorescent dye compounds used to analyze a particular cell or cell compartment embraces the pH of that cell or cell compartment is generally sufficient.

In certain embodiments, methods are provided for detecting a pH related intracellular process, the methods comprising:

(a) contacting one or more of the pH-sensitive fluorescent dye compounds disclosed herein with a cell to form a contacted cell;

(b) incubating the contacted cell to form an incubated solution;

(c) illuminating the incubated solution to form an illuminated solution; and (d) detecting fluorescent emissions from the illuminated solution;

wherein increased fluorescent emissions indicates activation of the intracellular process.

In certain embodiments, methods are provided for detecting a pH related intracellular process, the methods comprising:

(a) contacting one or more of the compositions provided herein with a cell to form a contacted cell;

(b) incubating the contacted cell to form an incubated solution;

(c) illuminating the incubated solution to form an illuminated solution; and (d) detecting fluorescent emissions from the illuminated solution;

wherein increased fluorescent emissions indicates activation of the intracellular process.

In certain embodiments, the intracellular process is the opening of an ion channel. More particular still, the ion channel is calcium.

In certain embodiments, the pH-sensitive fluorescent dye compound is internalized after incubation with the cytosol of the cell.

Certain embodiments provide a no-wash, no-quench assay for phagocytosis that is based on fluorogenic bioparticles comprising the pH-sensitive fluorescent dye compounds provided herein. Current protocols for measuring phagocytosis that use fluorescent bioparticles, require a trypan blue quenching step and several washing steps. These steps can introduce significant variability in the assay. To address this issue, provided herein is a no-wash phagocytosis kit, using *E. coli* bioparticles conjugated to a pH-sensitive fluorescent dye as described herein. These bioparticle conjugates are weakly fluorescent at extracellular pH. However, when added to phagocytic J774.2 murine macrophages, they become ingested into acidic compartments and fluoresce from within the cells, giving specific signals that meet or exceed the brightness of the Vybrant™ Phagocytosis Assay Kit (Life Technologies Corporation). Quantitation of the phagocytic index with these conjugates requires no wash or quenching steps, and uptake of the bioparticles is potently inhibited by cytochalaisin D, a known blocker of phagocytosis. The pH-sensitive fluorescent bioparticles described herein may be used in plate based, as well as imaging and flow cytometry assays of phagocytosis.

In certain embodiments, methods are provided for detecting phagocytosis of a carrier molecule in solution, the methods comprising:

(a) conjugating the carrier molecule to one or more of the pH-sensitive fluorescent dye compounds disclosed herein to form a carrier-dye conjugate;

(b) contacting the carrier-dye conjugate with a cell to form a contacted cell;

(c) incubating the contacted cell to form an incubated solution;

(d) illuminating the incubated solution to form an illuminated solution; and (e) detecting fluorescent emissions from the illuminated solution;

wherein fluorescent emissions indicate phagocytosis of the carrier molecule.

In certain embodiments, methods are provided for detecting phagocytosis of a carrier molecule in solution, the methods comprising:

(a) conjugating the carrier molecule to one or more of the compositions disclosed herein to form a carrier-dye conjugate;

(b) contacting the carrier-dye conjugate with a cell to form a contacted cell;

(c) incubating the contacted cell to form an incubated solution;

(d) illuminating the incubated solution to form an illuminated solution; and (e) detecting fluorescent emissions from the illuminated solution;

wherein fluorescent emissions indicate phagocytosis of the carrier molecule.

In particular embodiments, the carrier molecule is an *E. coli* bioparticle.

In certain embodiments, methods are provided for diagnosing or detecting a disease in a subject, the methods comprising:

(a) contacting a sample obtained from a subject suspected of having the disease with one or more of the pH-sensitive fluorescent dye compounds disclosed herein, to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to diagnose or detect the disease.

In certain embodiments, methods are provided for diagnosing or detecting a disease in a subject, the methods comprising:

(a) contacting a sample obtained from a subject suspected of having the disease with one or more of the compositions disclosed herein, to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to diagnose or detect the disease.

In certain embodiments, the disease is associated with the central nervous system. In certain embodiments, the disease is Alzheimer's disease (AD). In certain embodiments, the pH-sensitive fluorescent dye compound is conjugated to a carrier molecule associated with the disease. In certain embodiments, the pH-sensitive fluorescent dye compound is conjugated to β-amyloid or a fragment or thereof. Accordingly, certain embodiments provides a blood based assay for Alzheimer's disease, based on the phagocytosis of the pH-sensitive fluorescent dye compounds disclosed herein conjugated to β-amyloid protein.

In certain embodiments, the disease is associated with the immune system. In certain embodiments, the disease is associated with inflammation. In certain embodiments, the disease is cancer. In certain embodiments, the disease is associated with oxidative stress. In certain embodiments, the pH-sensitive fluorescent dye compound is conjugated to a carrier molecule associated with the disease.

In certain embodiments, methods are provided for detecting a target molecule capable of modulating a cellular process that affects the pH or directly affects the pH of a cell. In certain embodiments, the target molecule is a small molecule. In certain embodiments, the cell is a neuronal cell. In certain embodiments, the cell is a cancer cell. In certain embodiments, the cell is an immune cell.

In certain embodiments, methods are provided for detecting any one of the following with a pH-sensitive fluorescent dye compound as described herein: an antibody, protein, peptide, enzyme substrate, hormone, lymphokine, metabolite, receptor, antigen, hapten, lectin, avidin, streptavidin, toxin, carbohydrate, oligosaccharide, polysaccharide, nucleic acid, derivatized deoxy nucleic acid, DNA fragment, RNA fragment, derivatized DNA fragment, derivatized RNA fragment, nucleoside, nucleotide, natural drug, synthetic drug, virus particle, bacterial particle, virus component, yeast component, blood cell, blood cell component, plasma component, serum component, biological cell, neuronal cells, noncellular blood component, bacteria, bacterial component, natural or synthetic lipid vesicle, poison, environmental pollutant, polymer, polymer particle, glass particle, glass surface, plastic particle, plastic surface, polymer membrane, conductor or semiconductor comprising detecting a compound disclosed herein bound to said antibody, protein, peptide, enzyme substrate, hormone, lymphokine, metabolite, receptor, antigen, hapten, lectin, avidin, streptavidin, toxin, carbohydrate, oligosaccharide, polysaccharide, nucleic acid, derivatized deoxy nucleic acid, DNA fragment, RNA fragment, derivatized DNA fragment, derivatized RNA fragment, nucleoside, nucleotide, natural drug, synthetic drug, virus particle, bacterial particle, virus component, yeast component, blood cell, blood cell component, plasma component, serum component, biological cell, noncellular blood component, bacteria, bacterial component, natural or synthetic lipid vesicle, poison, environmental pollutant, polymer, polymer particle, glass particle, glass surface, plastic particle, plastic surface, polymer membrane, conductor or semiconductor.

In certain embodiments, methods are provided for detecting acidic or basic conditions comprising contacting a pH-sensitive fluorescent dye compound as described herein with a composition suspected of being acidic or basic and detecting the fluorescence of the pH-sensitive fluorescent dye compound as an indicator of said acidic or basic conditions. In certain embodiments, the composition being tested comprises an intracellular environment.

Accuracy for the general means of measuring pH may be further increased by using a plurality of the pH-sensitive fluorescent dye compounds provided herein having different fluorescent responses. In certain embodiments, two or more pH-sensitive fluorescent dye compounds according to the present invention may be used, optionally bonded to identical carrier molecules or solid supports, or a pH-sensitive fluorescent dye compound as disclosed herein and another different dye. In certain embodiments, the second fluorescent dye has a positive fluorescence response with increasing pH (i.e., that the intensity of fluorescence exhibited by the dye or complex increases with increasing pH). It is preferable that the two or more dyes have overlapping titration ranges, and more preferably the different dyes or conjugates have pKa values within about 1 unit of each other. The intensity of fluorescence of each dye or conjugate is then measured, and pH determined by calculating the ratio of the fluorescence intensity of the first compound to the fluorescence intensity of the second compound and comparing the value obtained to a calibration curve.

In certain embodiments, the pH-sensitive dye compounds may be used to analyze the kinetics of migration of a species into or through a cell or cell compartment. This may be done by monitoring the intensity of fluorescence of a pH-sensitive dye compound over a time interval. Where pH is known, the pH-sensitive dye compound should be selected so as to have a pKa in the range between the pH at the starting point and the pH at the end point of the pathway to be analyzed. In some cases it may be desirable to use a plurality of pH-sensitive dye compounds having a variety of pKa values, with each dye or complex tuned to a different portion of the pathway to be analyzed.

In certain embodiments, methods are provided for using a pH-sensitive fluorescent dye compound, dye conjugate, or composition provided herein for analysis or detection. More particularly, the detection may be performed by optical means. In certain embodiments, the fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes.

In certain embodiments, the sample or medium in which a pH-sensitive fluorescent dye compound provided herein is present is illuminated with a wavelength of light selected to give a detectable optical response, and observed with a means for detecting the optical response. Equipment that is useful for illuminating the pH-sensitive fluorescent dye compounds and compositions disclosed herein includes, but is not limited to, hand-held ultraviolet lamps, mercury arc lamps, xenon lamps, lasers and laser diodes. These illumination sources are optically integrated into laser scanners, fluorescence microplate readers or standard or microfluorometers.

The pH-sensitive fluorescent dye compounds, dye conjugates, and compositions disclosed herein may, at any time after or during an assay, be illuminated with a wavelength of light that results in a detectable optical response, and observed with a means for detecting the optical response. Upon illumination, such as by an ultraviolet or visible wavelength emission lamp, an arc lamp, a laser, or even sunlight or ordinary room light, the fluorescent compounds, including those bound to the complementary specific binding pair member, display intense visible absorption as well as fluorescence emission. Selected equipment that is useful for illuminating the fluorescent pH-sensitive fluorescent dye compounds disclosed herein include, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds disclosed herein and a second fluorophore with detectably different optical properties, typically by distinguishing the fluorescence response of the fluorescent compounds of the invention from that of the second fluorophore. Where a sample is examined using a flow cytometer, examination of the sample optionally includes isolation of particles within the sample based on the fluorescence response by using a sorting device. In certain embodiments, the illumination source is used to form a covalent bond between the present pH-sensitive fluorescent dye compound and an analyte of interest. In this instance the pH-sensitive fluorescent dye comprises a photoactivatable reactive group, such as those discussed above.

Kits:

In certain embodiments, kits are provided for determining the pH of a sample comprising:

(a) one or more of the pH-sensitive fluorescent dye compounds described herein;

(b) one or more containers; and optionally (c) instructions for determining the pH of the sample.

In certain embodiments, kits are provided for determining the pH of a sample comprising:

(a) one or more of the pH-sensitive fluorescent dye compositions described herein;

(b) one or more containers; and optionally (c) instructions for determining the pH of the sample.

In certain embodiments, the kits further comprise one or more of the following: a buffering agent, a purification medium, a vial comprising the sample, or an organic solvent.

As used herein, the term "kit" refers to a packaged set of related components, typically one or more pH-sensitive fluorescent dye compounds or compositions. In certain embodiments, the kits disclosed herein comprise one or more of the pH-sensitive fluorescent dye compounds described herein, one or more carriers suitable for in vitro or in vivo applications, and one or more containers in which to store the one or more pH-sensitive fluorescent dyes and/or one or more carriers, such as solvents, buffers, stabilizers, pH adjusting agents, etc. The kit optionally contains instructions for how to prepare the one or more pH-sensitive fluorescent dyes or how to prepare a composition containing the one or more pH-sensitive fluorescent dye, and how to administer the dye or composition containing the dye. In certain embodiments, the kit comprises instructions for performing an assay that detects the pH or pH changes in samples. In certain embodiments, the assay is an in vitro assay. In certain embodiments, the assay is an in vivo assay. The kit may further comprise one or more pieces of equipment to administer the dye compound, or composition comprising the pH-sensitive fluorescent dye compound including, but not limited to, syringes, pipettes, pipette bulbs, spatulas, vials, syringe needles, and various combinations thereof.

In certain embodiments, the kits provided herein comprise indicator solutions or indicator "dipsticks", blotters, culture media, cuvettes, and the like. In certain embodiments, the kits provided herein comprise indicator cartridges (where a kit component is bound to a solid support) for use in an automated detector. In certain embodiments, the kits provided herein further comprise molecular weight markers, wherein said markers are selected from phosphorylated and non-phosphorylated polypeptides, calcium-binding and non-calcium binding polypeptides, sulfonated and non-sulfonated polypeptides, and sialylated and non-sialylated polypeptides. In certain embodiments, the kits provided herein further comprise a member selected from a fixing solution, a detection reagent, a standard, a wash solution, and combinations thereof.

Synthesis and Processes of Preparation of the pH-Sensitive Fluorescent Dye Compounds In certain embodiments, processes are provided for synthesizing a compound of structural formula (I):

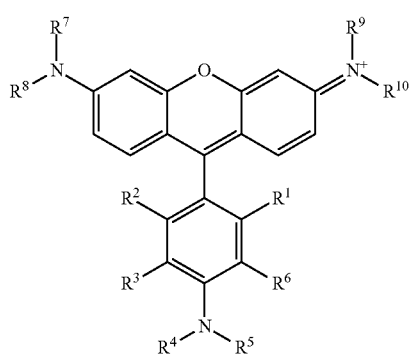

(I)

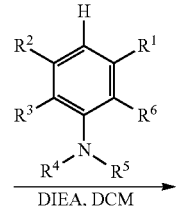

the process comprising:
contacting a compound of structural formula (III):

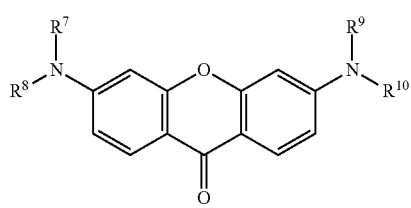

(III)

with a compound of structural formula (IV):

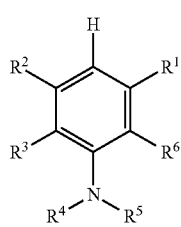

(IV)

to form a compound of structural formula (I),
wherein $R^1$, $R^2$, $R^3$, $R^4$, $R^5$, $R^6$, $R^7$, $R^8$, $R^9$ and $R^{10}$ are as previously defined.

An exemplary reaction scheme is shown in detail below:

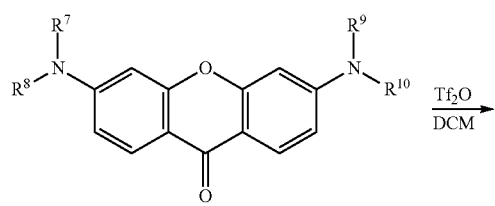

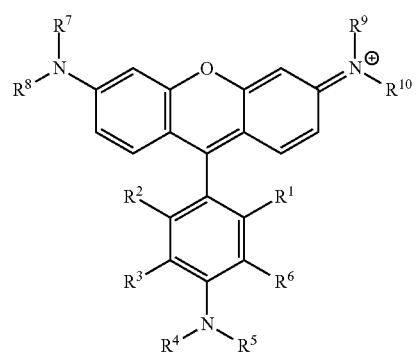

-continued wherein $R^1$, $R^2$, $R^3$, $R^4$, $R^5$, $R^6$, $R^7$, $R^8$, $R^9$, $R^{10}$ are as described herein.

In certain embodiments, any one of the above methods of synthesis further comprises a purifying step. In certain more particular embodiments, the purifying step comprises at least one of: column chromatography, trituration, recrystallization, filtration, or aqueous separation.

A detailed description of the present teachings having been provided above, the following examples are given for the purpose of illustrating the invention and shall not be construed as being a limitation on the scope of the invention or claims.

EXAMPLES

Referring to the examples that follow, pH-sensitive fluorescent dye compounds disclosed herein were synthesized using the methods described herein, or other methods, which are known in the art.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

Chemical Synthesis of the Fluorescent pH-Sensitive Dye Compounds Disclosed Herein Example 1

Preparation of Compound (3)

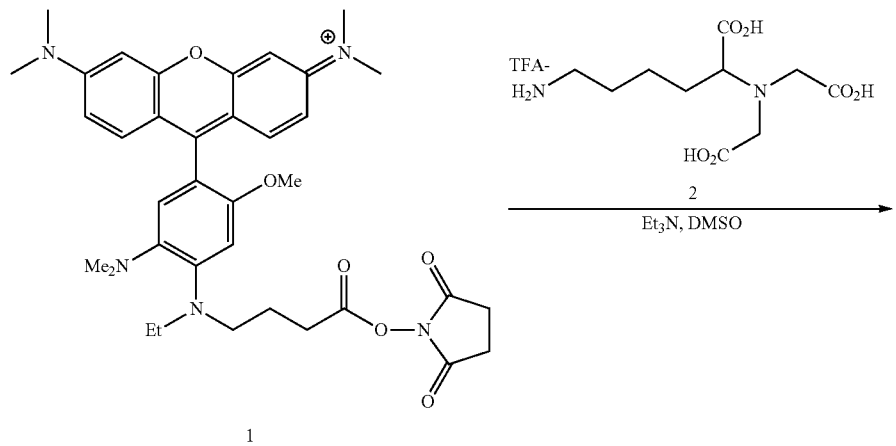

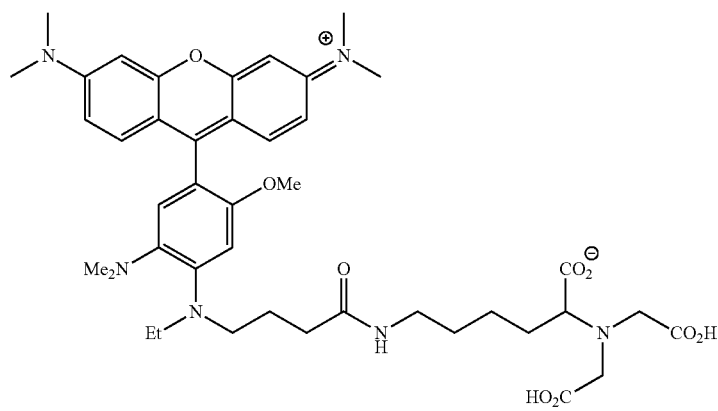

2-(bis(carboxymethyl)amino)-6-(4-((2-(dimethylamino)-4-(6-(dimethylamino)-3-(dimethyliminio)-3H-xanthen-9-yl)-5-methoxyphenyl)(ethyl)amino)butanamido)hexanoate (Compound 3)

To a solution of Compound (2) (24.0 mg, 0.065 mmol) and triethylamine (45 µL, 0.325 mmol) in DMSO (1 mL) was added Compound (1) (40 mg, 0.059 mmol) dissolved in DMF (1 mL) and the mixture was stirred at room temperature for 18 hours. All volatile materials were removed by vacuum pump. The crude mixture was treated with 1 mL of water, and was purified by chromatography on C-18 (Biotage SNAP 12 g, MeOH:H$_2$O=0:100~30:70) to afford Compound (3) (38 mg, 81%) as a dark purple powder. H$^1$ NMR (MeOD): 7.40 (d, 2H), 7.10 (m, 4H), 6.91 (2H, s), 3.75 (s, 3H), 3.65 (q, 4H), 3.43 (m, 2H), 3.40 (m, 2H), 3.30 (s, 12H), 3.18 (m, 2H), 2.75 (s, 6H), 2.23 (m, 2H), 1.90 (b, 4H), 1.55 (m, 4H), 1.23 (t, 2H,), 1.10 (t, 3H).

Example 2

Preparation of Compound (4)

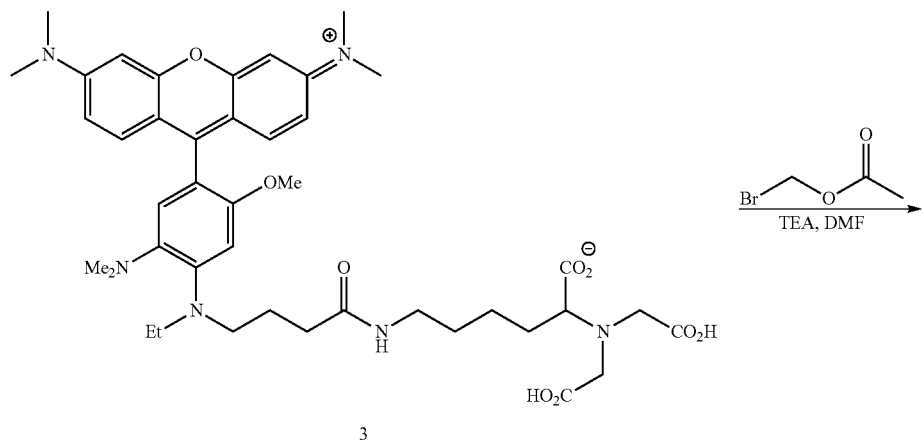

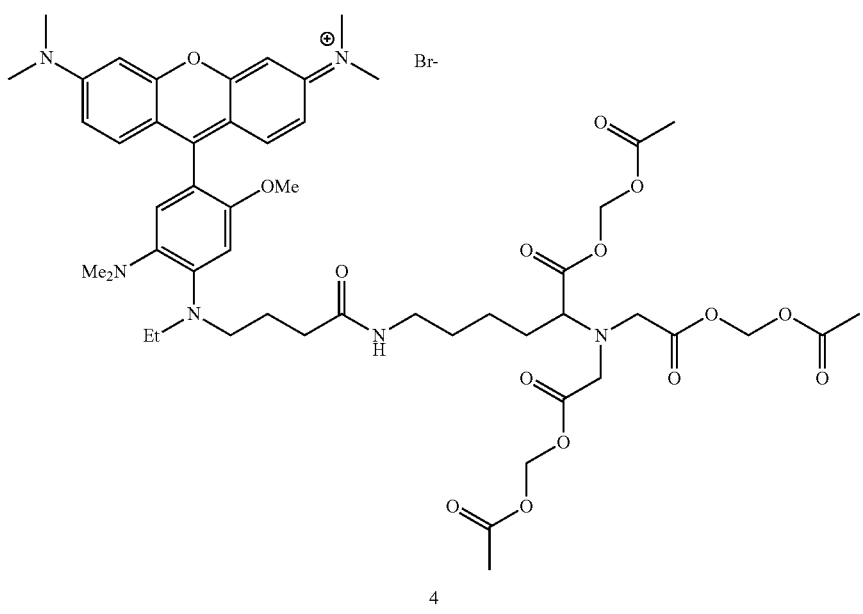

N-(9-(4-((8-(2-(acetoxymethoxy)-2-oxoethyl)-9-((acetoxymethoxy)carbonyl)-2,6,15-trioxo-3,5-dioxa-8,14-diazaoctadecan-18-yl)(ethyl)amino)-5-(dimethylamino)-2-methoxyphenyl)-6-(dimethylamino)-3H-xanthen-3-ylidene)-N-methylmethanaminium (Compound 4)

Compound (3) (38 mg, 0.048 mmol) was dissolved in DMF (2 mL). Triethylamine (50 μL, 0.336 mmol) was added into the solution. Bromomethyl acetate (0.05 mL, 0.48 mmol) was added dropwise, the white smoke was formed during addition. The mixture was stirred at room temperature for 1 hour. All volatile materials were removed and the residue was dried by vacuum pump. The resulting residue was dissolved in chloroform (20 mL) and washed with 1:1 saturated NaHCO$_3$-water, the organic layer was dried and concentrated, purified by chromatography on silica gel column (Biotage, SNAP 25 g, MeOH: chloroform=0-10%) to afford Compound (4) (40 mg, 77%) as a dark purple solid. H$^1$ NMR (d6-DMSO) 7.80 (t, 1H), 7.30 (d, 2H), 7.15 (d, 2H), 6.89 (s, 2H), 6.75 (d, 2H), 5.60 (m, 6H), 4.00 (s, 4H), 3.62 (s, 3H), 3.60 (q, 4H), 3.40 (m, 2H), 3.20 (s, 12H), 3.00 (m, 2H), 2.60 (s, 6H), 2.10 (m, 2H), 2.00 (s, 9H), 1.70 (s, 2H), 1.70 (m, 2H), 1.50 (m, 2H), 1.30 (m, 2H), 1.10 (m, 2H), 1.0 (t, 3H). LCMS: 1007.1 (M+1).

Example 3

Preparation of Compounds (7) and (8)

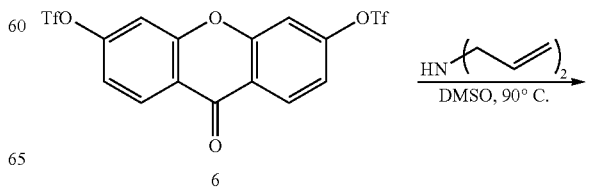

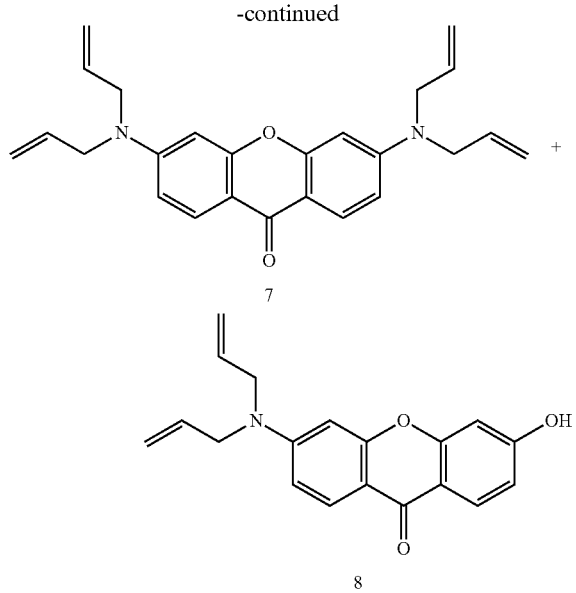

Compound (6) (9.00 g, 18.3 mmol, see, Wu et al., *Org. Lett.* 10:1779-1782 (2008), herein incorporated by reference in its entirety) was treated with DMSO (56 mL) and diallylamine (21.2 g, 219 mmol) at room temperature, and the mixture was heated to 90° C. for 36 hours. The mixture was cooled to room temperature, and quenched by adding water (250 mL). The product was extracted with ethyl acetate (200 mL×3). The combined organic layers were washed by water (200 mL×2), brine (300 mL), dried by MgSO₄, and evaporated. The crude product was purified by chromatography on silica gel column (Biotage, SNAP 340 g, 6.5×18 cm, ethyl acetate:hexanes=1:2) to give Compound (7) (3.30 g, 47%, white solid), and Compound (8) (1.10 g, 20%, pale yellow solid).

Example 4

Preparation of Compound (9)

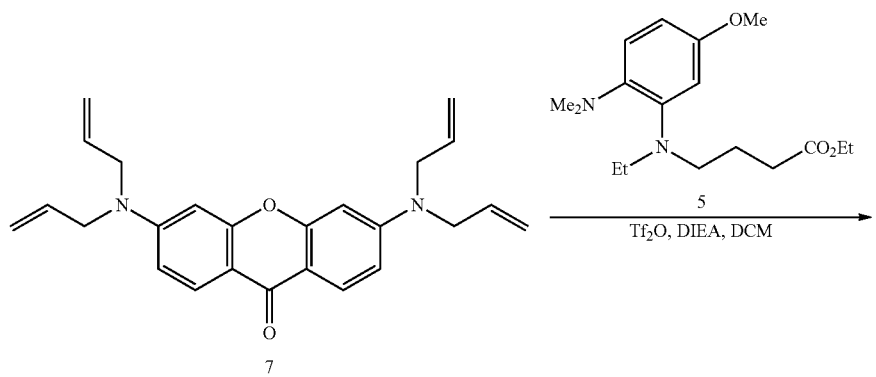

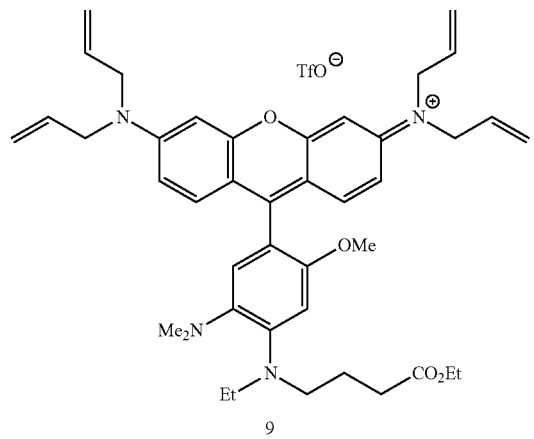

Compound (7) (149 mg, 0.386 mmol) was treated with anhydrous DCM (5 mL) and Tf$_2$O (80 μL, 0.476 mmol), and the mixture was stirred at room temperature. After 30 min stirring, Compound (5) (150 mg, 0.486 mmol) in DCM (2 mL) and DIEA (120 μL, 0.689 mmol) were added. The reaction was stirred at room temperature for 16 hours. Evaporation gave a crude product. The crude product was purified by chromatography on silica gel column (Biotage, SNAP 25 g, 2.5×8 cm, MeOH:CHCl$_3$=1:10 1:4) to give Compound (9) (200 mg, 62%) as a purple gummy material.

Example 5

Preparation of Compounds (14) and (15)

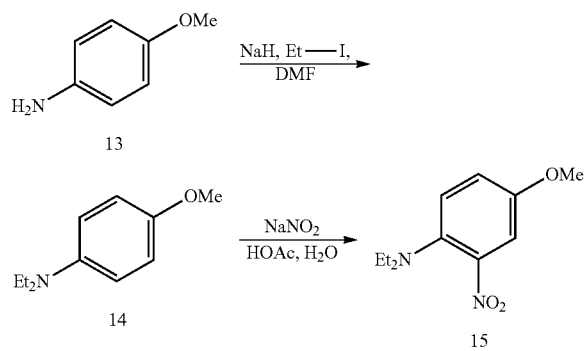

A solution of 4-methoxyaniline (13) (10.0 g, 81.2 mmol) in DMF (100 mL) was treated with 60% NaH (8.10 g, 203 mmol) and iodoethane (26.0 mL, 235 mmol). The temperature of the mixture was kept at 0° C. by ice bath in first 3 hour stirring. The ice bath was removed and the mixture was stirred at room temperature for another 12 hours. Water (200 mL) was added to quench this reaction. The product was extracted by ethyl acetate (200 mL×3). The combined organic layers were washed by water (200 mL×5), brine (200 mL), and dried over sodium sulfate. Filtration and evaporation gave Compound (14) (16.2 g, ~100%) as a dark green oil.

To a solution of N,N-diethyl-4-methoxyaniline (14) (6.0 g, 27 mmol) in water (500 mL) and acetic acid (50 mL) was added a solution of NaNO$_2$ (3.8 g, 55 mmol) in water (70 mL) dropwise within 30 min at room temperature. The reaction mixture was stirred at room temp for 3 hours. The product was extracted by ethyl acetate (150 mL×3). The combined organic layers were washed by 1M KOH (100 mL×4), brine (100 mL) and dried over anhydrous sodium sulfate. Filtration and evaporation gave a crude product as dark red oil. The crude product was purified by chromatography on silica gel column (Biotage, SNAP 100 g, 3.5×16 cm, from 15% CHCl$_3$ in hexanes to 100% CHCl$_3$) to give Compound (15) (4.90 g, 81%) as a dark red oil.

Example 6

Preparation of Compounds (16) and (17)

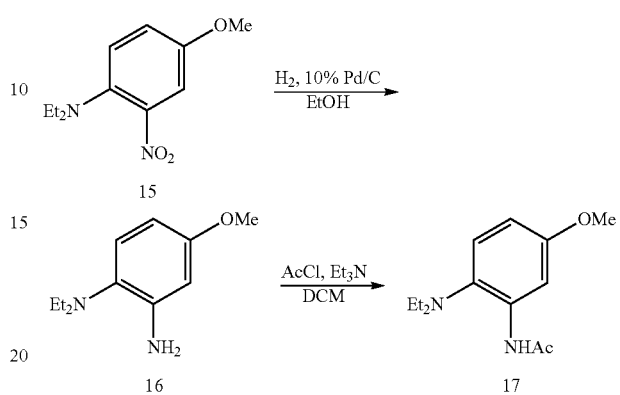

To palladium on activated charcoal (650 mg) was added ethanol (15 mL) under argon carefully. A solution of Compound (15) (5.30 g, 23.6 mmol) in ethanol (75 mL) was treated with the palladium suspension solution by a pipet. The solution was equipped with a 3-way stopcock attached by a 3 L balloon filled with hydrogen. The solution was evacuated and refilled with hydrogen carefully three times. The solution was stirred under hydrogen atmosphere for 18 hours. Filtration through a Celite pad was performed to remove palladium, and the filtrate was concentrated to dryness to get crude product. The crude product was purified by chromatography on silica gel column (Biotage, SNAP 100 g, 3.5×16 cm, ethyl acetate:hexanes=1:4) to give Compound (16) (4.14 g, 90%, as light brown oil).

A solution of Compound (16) (4.14 g, 21.3 mmol) in DCM (60 mL) was treated with acetyl chloride (1.80 mL, 25.6 mmol) and triethylamine (4.44 mL, 32.0 mmol) at 0° C. The mixture was stirred at 0° C. for 30 min, and quenched by adding MeOH (1 mL). The mixture was diluted by ethyl acetate (300 mL) and the solution was washed by water (200 mL), brine (150 mL), and dried over anhydrous sodium sulfate. Evaporation gave pure crude product of Compound (17) (4.73 g, 94%) as a light brown oil. No further purification was required.

Example 7

Preparation of Compounds (18) and (19)

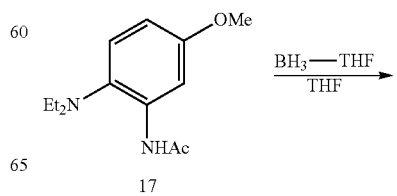

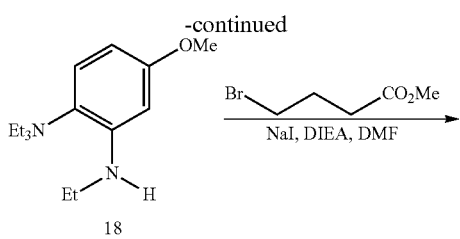

A solution of Compound (17) (4.73 g, 20.0 mmol) in anhydrous THF (15 mL) was treated with BH₃-THF (60 mL of 1M solution in THF, 60 mmol) carefully. The mixture was heated to reflux for 2 hours and cooled to room temperature. MeOH (60 mL) was added to the solution slowly to quench extra amount of borane complex at room temp, and the mixture was heated to reflux for 10 min. The solution was cooled to room temperature, and evaporated to dryness. The residue was dissolved in 300 mL of ethyl acetate, and washed by saturated sodium bicarbonate (150 mL×2), brine (100 mL), and dried over anhydrous sodium sulfate. Evaporation gave pure crude product of Compound (18) (4.12 g, 93%) as a light brown oil. No further purification was required.

A solution of Compound (18) (4.06 g, 18.3 mmol) in 40 mL of DMF was treated with methyl 4-bromobutanoate (9.23 mL, 73.1 mmol), NaI (1.36 g, 9.07 mmol), and DIEA (9.44 mL, 54.2 mmol), and the mixture was heated to 100° C. for 22 hours. The reaction was cooled to room temperature, 200 mL of water were added, and extracted by ethyl acetate (150 mL×3). The combined organic layers were washed by water (150 mL×3), brine (100 mL), dried over anhydrous sodium sulfate, and evaporated to give crude product. The crude product was purified by chromatography on silica gel column (Biotage, SNAP 100 g, 3.5×16 cm, ethyl acetate:hexanes=1:4) to give Compound (19) (4.60 g, 79%) as light brown oil.

Example 8

Preparation of Compound (20)

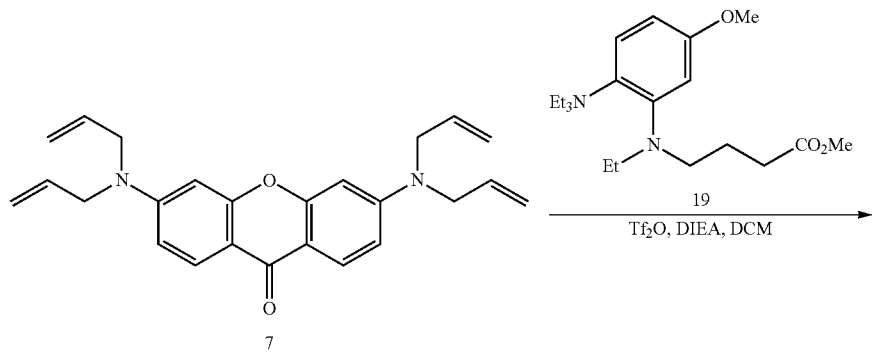

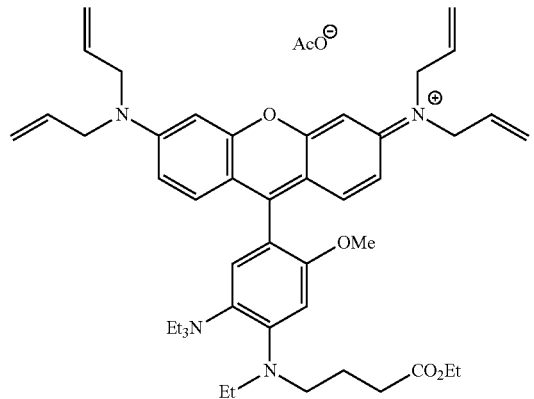

Compound (7) (2.15 g, 5.54 mmol) was treated with anhydrous DCM (50 mL) and Tf$_2$O (0.94 mL, 0.5.60 mmol), and the mixture was stirred at room temperature. After 30 min of stirring, Compound (19) (2.13 g, 6.65 mmol) in DCM (15 mL) and DIEA (1.25 mL, 7.18 mmol) were added. The reaction was stirred at room temperature for 22 hours. Evaporation gave crude product. The crude product was purified by chromatography on silica gel column (Biotage, SNAP 100 g, 3.5×16 cm, H$_2$O:MeCN:HOAc=1:10:0.1~1:6:0.1) to give Compound (20) (2.58 g, 62%) as a purple gummy material.

Example 9

Preparation of Compound (25)

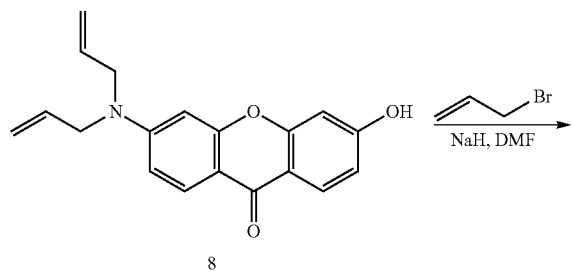

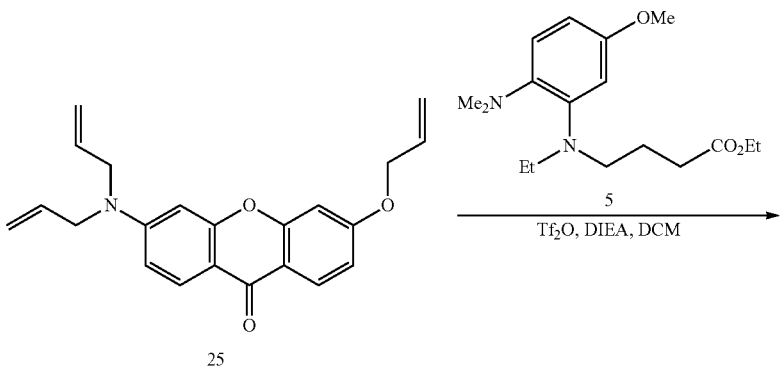

A solution of Compound (8) (170 mg, 0.553 mmol) in DMF (5 mL) was treated with 60% NaH (33.0 mg, 0.825 mmol) and allyl bromide (134 mg, 1.11 mmol) at 0° C. The mixture was allowed warm to room temperature and stirred overnight (~16 hours). The reaction was quenched by water (20 mL). The solution was extracted by ethyl acetate (30 mL×3). The combined organic layers were washed by water (30 mL×3), brine (50 mL), dried over magnesium sulfate and evaporated to give Compound (25) (210 mg, ~100%) as pale yellow solid. No further purification was required.

Example 10

Preparation of Compound (29)

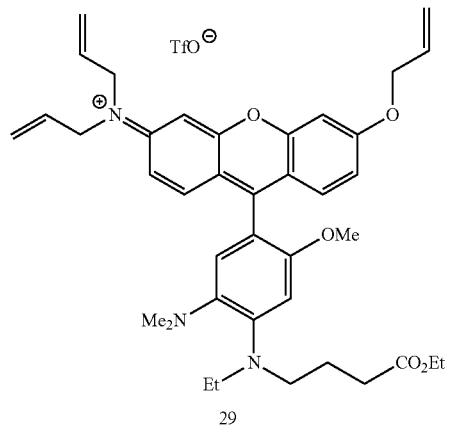

Compound (25) (210 mg, 0.605 mmol) was treated with anhydrous DCM (8 mL) and Tf$_2$O (121 µL, 0.719 mmol), and the mixture was stirred at room temperature. After 30 min stirring, Compound (5) (239 mg, 0.774 mmol) in DCM (6 mL) and DIEA (160 µL, 0.910 mmol) were added. The reaction was stirred at room temperature for 20 hours. Evaporation gave crude product. The crude product was purified by chromatography on silica gel column (Biotage, SNAP 50 g, 3.5×8.5 cm, MeOH:CHCl$_3$=1:10 1:4) to give Compound (29) (412 mg, 87%) as a gray gummy material.

Example 11

Preparation of EGF Conjugate of Compound (4)

0.6 mg of a 5 mg/ml EGF stock solution (120 µL, 0.098 µmol) was added to a 2 mL vial. 0.6 mg of Compound (4) (0.88 mol) was dissolved in 100 µL of DMSO, and 23 µL of the solution was added into the vial with EGF. The dye to protein molar ratio was ~2.50 µL of Triethylamine was dissolved in 0.5 mL of DMSO. 6 µL of the triethylamine solution was added to the EGF solution and stirred, covered, for 24 hours. About 1/10 volume of 1.5 M hydroxylamine (pH 8.0) was added to stop the reaction and stirred for about 30 minutes at room temperature. The conjugate was purified on a P-2F column (15×1 cm) with PBS (pH 7.2). 3-6 fractions were collected containing 1-2 mL each and run on a TLC in CMA (70:25:5) to confirm the absence of free dye and processed by HPLC to check for unlabeled EGF. Fractions containing free dyes and fractions containing unlabeled EGF were discarded. Fractions containing no free dye and no unlabeled EGF were combined as the final product. The A566 nm/A280 nm was measured and the conjugate concentration was determined (80 µg/ml) and degree of substitution (DOS=1) by absorbance. BSA powder was added to the conjugate solution (final concentration of 1%) and stirred to gently dissolve. The EGF conjugate was frozen in dry ice for at least 1 hour and lyophilized for at least 18 hours.

Biological Application Examples of the Fluorescent pH-Sensitive Dye Compounds

Example 12

Correlation Between pH and Fluorescence of the pH-Sensitive Dye Compounds Provided Herein The fluorogenic nature of the pH-sensitive fluorescent dye compounds described herein makes them very useful for studying a variety of internalization processes that occur in cells, such as phagocytosis and endocytosis. This is because upon internalization, there is a drop in pH inside the phagosome or endosome which results in an increase of fluorescence from the pH-sensitive fluorescent dye compounds. Conjugation of the pH-sensitive fluorescent dye compounds to biomolecules of interest provide for convenient assays of internalization of these molecules. Examples include transferrin, EGF and low-density lipoprotein (LDL) for studying receptor-mediated endocytosis, and labeled bioparticles, such as *E. coli, Staphylococcus*, and zymosan for studying phagocytosis. Assays using these fluorogenic bioconjugates offer significant advantages over existing techniques due to the fact that the pH-sensitive fluorescent dye compounds are relatively non-fluorescent at the neutral pH outside the cell. This reduces or eliminates the need for wash steps and quencher dyes normally needed to reduce background signal from bioconjugates outside of the cells.

Figure 3:
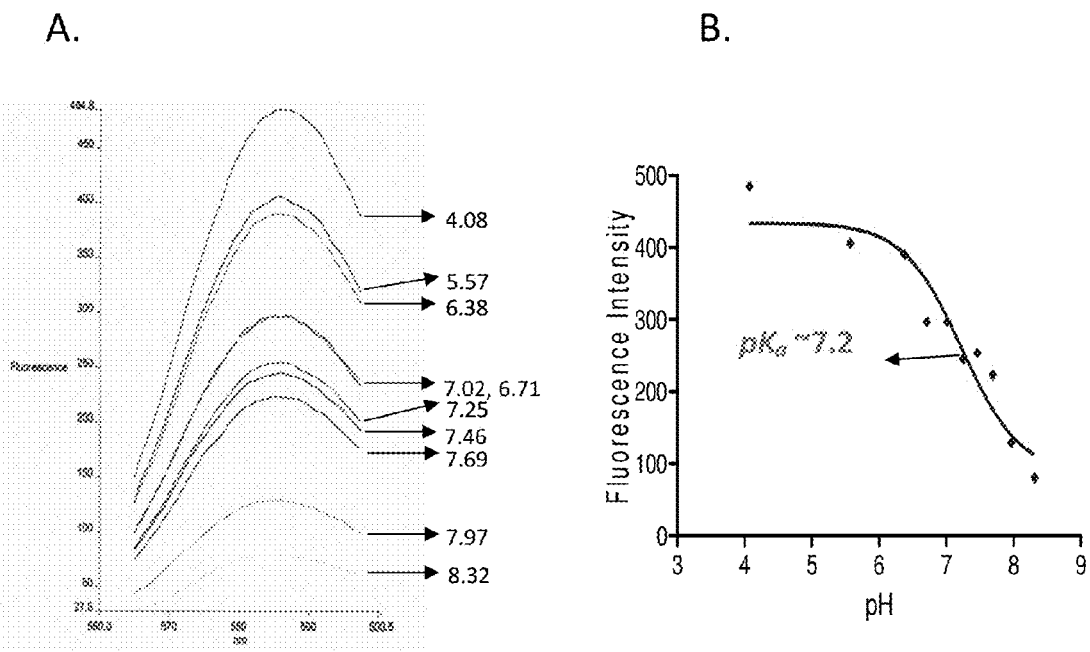
FIG. 3 graphically shows the correlation of pH with fluorescence for Compound (1). Panel A shows the fluorescence intensity of Compound (1) as a function of pH. Panel B shows the pKa of Compound (1).

The study of the fluorescent response of the pH-sensitive fluorescent dye compounds to changes in pH was performed in aqueous buffers (in concentrations around 10 µmol/mL). The results of the titrations for Compound (1) are shown in FIG. 3.

Example 13

Intracellular Uptake of the pH-Sensitive Fluorescent Dye Compounds

Figure 2:
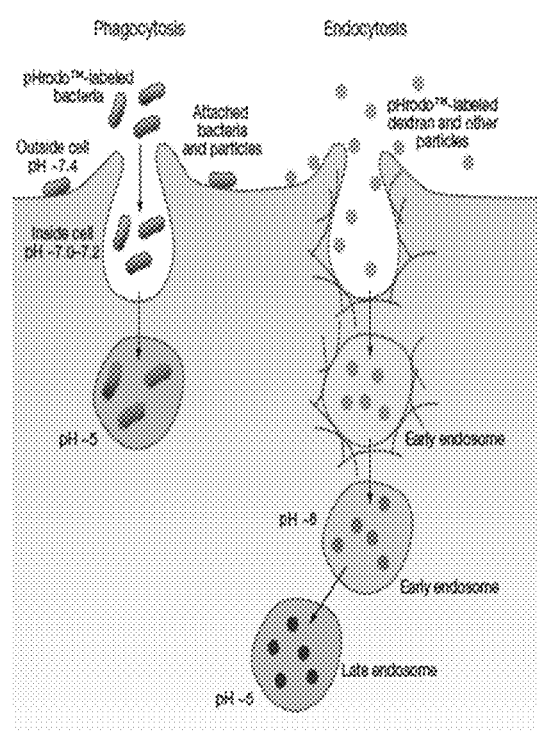
FIG. 2 describes cellular uptake of pH-sensitive fluorescent dye compounds. Panel A is a schematic representation of cellular uptake of pH-sensitive fluorescent dye-conjugated compounds including dye-conjugated bacteria for monitoring phagocytosis and dye-conjugated particles for monitoring endocytosis, using the compounds and methods according to embodiments disclosed herein. Panel B is a fluorescence micrograph showing cells that have internalized a pH-sensitive fluorescent dye compound according to certain embodiments of the present teachings.
Figure 2:
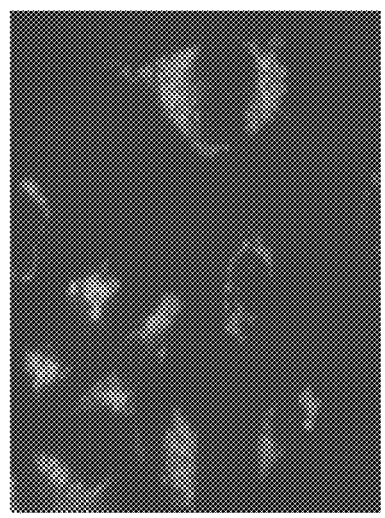

FIG. 2, Panel B shows cellular internalization of Compound (1). Cells were imaged using standard fluorescent illumination and microscopy.

Example 14

Live Cell Phagocytosis/Endocytosis with pH-Sensitive Fluorescent Dye Conjugates

Figure 4:
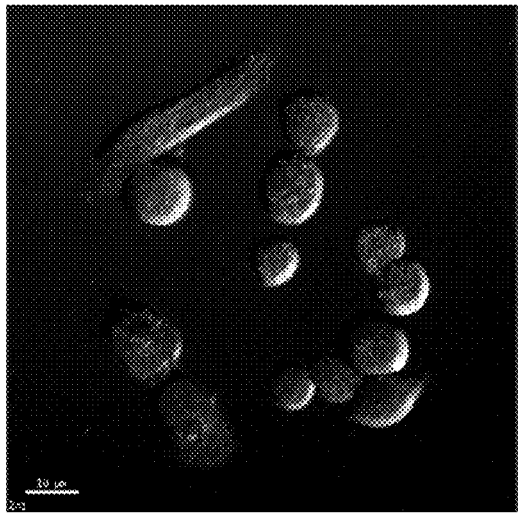
FIG. 4 shows internalization of EGF conjugated to Compound (4). The left panel shows cells pretreated with EGF only and the right panel shows cells treated with dye-conjugated EGF.
Figure 4:
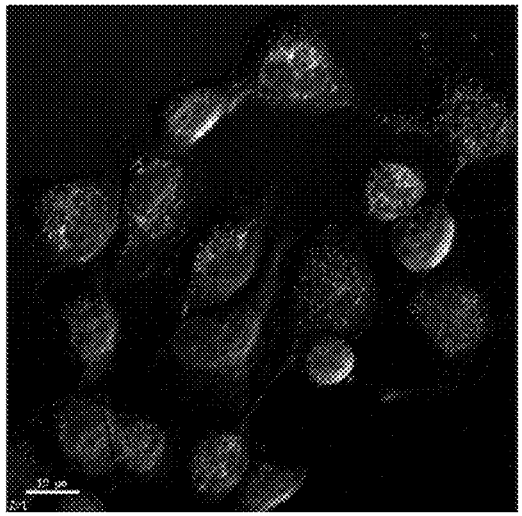

A 431 cells were grown in complete medium on 35 mm poly-D-lysine coated glass bottom culture dishes from MatTek. On the day of the assay, cells were rinsed once with LCIS+1% BSA (Live Cell imaging solution, Cat# A14291DJ, Life Technologies, Carlsbad, Calif.) and placed at 37° C. Control dishes received LCIS; EGF pretreatment dishes received 10 µg/mL unlabeled EGF in LCIS. Cells were incubated at 37° C. for 30 minutes. Cells were then cooled to 4° C. on ice for 10 minutes. Compound (4)-labeled EGF was added to the dishes 1:10 at 5 µg/mL from a 50 µg/mL stock in LCIS. These dishes were incubated on ice for 30 minutes, then washed 2× with cold LCIS and allowed to warm to 37° C. for 60 minutes before imaging with standard TRITC and FITC filter sets on a DeltaVision Core microscope. Cells pretreated with unlabeled EGF showed no signal owing to the occlusion of dye-labeled EGF binding sites and internalization of EGF receptors by excess unlabeled EGF. Specific signal from untreated plates was from dye-labeled EGF internalization. All images were matched for gain and exposure times. FIG. 4 shows internalization of EGF conjugated to Compound (1). The left panel shows cells pretreated with EGF and the right panel shows cells treated with dye-conjugated EGF.

pH-sensitive fluorescent dye compounds were made up in LCIS from 5 and 10 mM DMSO stocks respectively, and loaded for imaging as follows:

10 mL Loading Buffer, Compound (4):

10 µL Compound (4) from a 5 mM DMSO stock was added to 100 µL Powerload and mixed. 10 mL LCIS was added to this solution for final concentration of Compound (4) of 5 µM.

Figure 5:
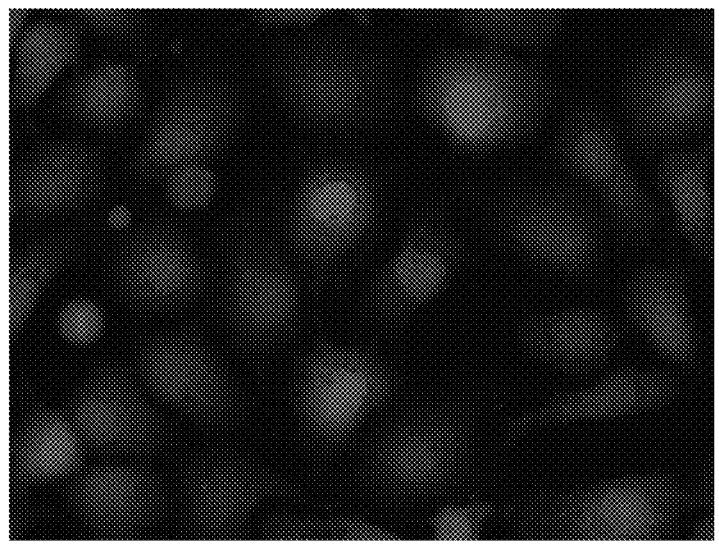
FIG. 5 shows internalization of Compound (4) in cells.

Cells were cultured on 35 mm MatTek glass bottom dishes. For loading, cells were rinsed 1× with LCIS and replaced with loading buffer described above. Cells were incubated at 37° C. for 60 minutes, then rinsed 2× with LCIS and imaged with standard TRITC or FITC filter sets. (see FIG. 5).

Figure 6:
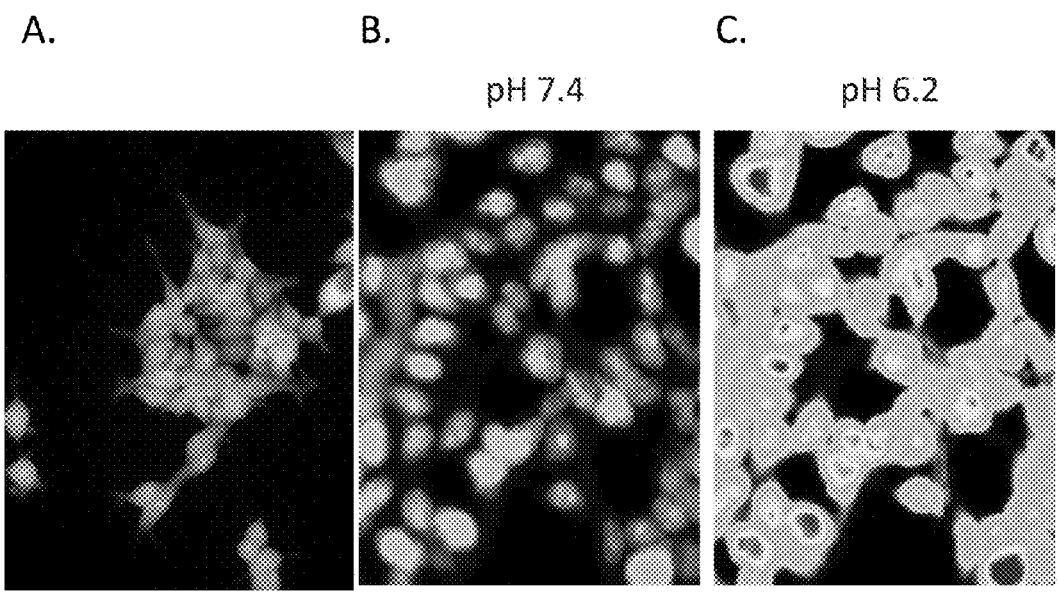
FIG. 6 shows the change of fluorescent signal from the Compound (4) located inside the cell as the external pH changes that reflects the equilibration of protons through the nigericin pores in the cellular membrane.
Figure 7:
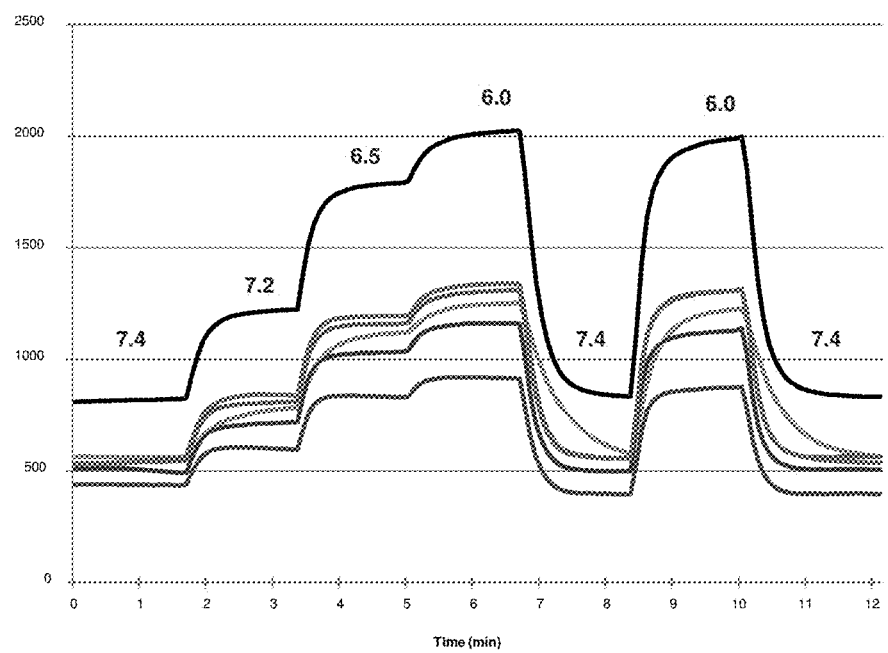
FIG. 7 shows cycling of cytosolic pH as measured by fluorescence of cells labeled with Compound (4).

Cells were cultured and loaded as described above with Compound (4). This solution was removed from the cells and replaced with potassium LCIS pH 7.4 standard and imaging experiments begun with cells under constant perfusion by potassium LCIS pH standards of pH 7.4, 7.2, 6.5, and 6.0. As the external pH was changed, the signal from the dye inside of the cells changed to reflect the equilibration of protons through the nigericin pores in the membrane. (Nigericin and valinomycin added at 10 µM each from DMSO stock.) Images of Compound (4) AM loaded cells at pH 7.4 and 6.0 are shown in FIG. 6. Functional kinetic responses from individually selected cells in the sample are shown in FIG. 7 as the pH was changed from 7.4 to 6.0 and back.

Example 15

Antibody Labeling Using pH-Sensitive Fluorescent Dyes

A freshly prepared 10 mM DMSO solution of Compound (1)-maleimide was added to an IgG solution (6 mg/mL) in PBS buffer at pH 7.0-7.5 in sufficient amount to give 10-20 moles of Compound (1) for each IgG molecule. The reaction was allowed to proceed for approximately 2 hours at which time the reaction mixture was poured on to a pre-packed Sephadex G-25 column. The column was eluted with PBS buffer to collect purified conjugated IgG. TLC analysis of a small aliquot (~5 µL) of the purified IgG indicated no free dye in the conjugate solution. The degree of labeling (DOL) was determined through a typical absorbance reading.

TABLE 4

| Dye-conjugated IgG | | |
| --- | --- | --- |
| Compound | Moles of dye/IgG molecule | Observed DOL |
| 4 | 10 | 2.1 |
| 4 | 20 | 2.93 |

Figure 8:
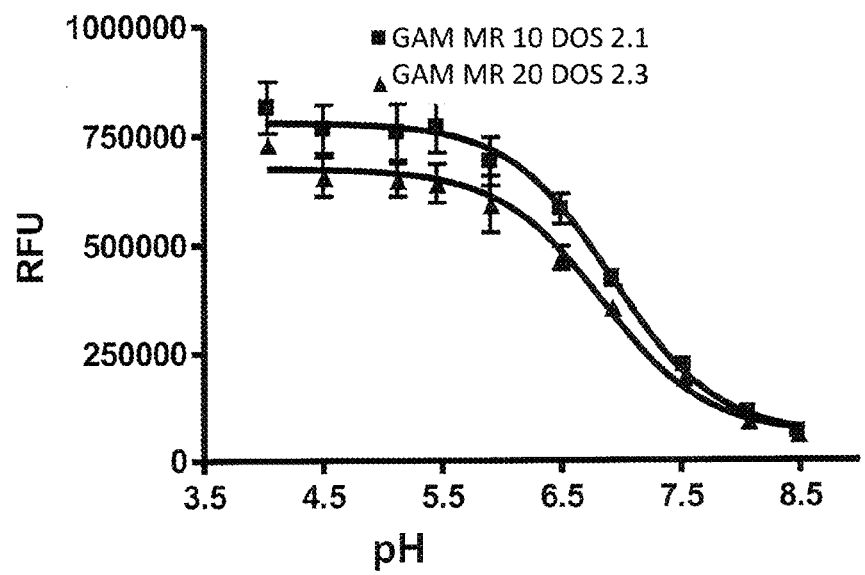
FIG. 8 shows the pH activation of fluorescent signal from IgG conjugates (IgG conjugated to Compound (1)).

Labeled IgGs were collected from the column and checked for purity via thin layer chromatography, to insure that all free dye was separated from the labeled IgG. These samples were diluted 1:10 to final concentrations of 10-100 µg/mL into a series of pH standard solutions from pH 4 to pH 9 and transferred into a 96 well microplate and scanned for fluorescence in a Molecular Devices FlexStation 384 plate reader. As can be seen in FIG. 8, relative fluorescence units (RFU) on the y-axis demonstrate the pH activation of fluorescent signal from the IgG conjugates, increasing signal with decreasing pH. pKa (midpoint) values near 6.8 of the conjugated antibodies track closely with the signal from the pH-sensitive fluorescent dyes.

Example 16

Labeling of Transferrin with pH Sensing Dyes

All materials are from Life Technologies Corp. (Carlsbad, Calif.) unless otherwise stated. Dissolve transferrin from human serum (Sigma, T4132) in 0.1 M $NaHCO_3$, pH 8.3, to a concentration of 10 mg/mL. Make a 10 mg/mL solution of the succinimidyl ester of the pH-sensitive fluorescent dye compound in dry DMSO and sonicate briefly to aid in dissolution of the dye. Add a 10 to 30-fold molar excess of the reactive dye solution to the transferrin solution dropwise while stirring. Note that the volume of dye added depends on the specific dye and the amount of transferrin to be labeled. Protect the reaction vessel from light and stir for ~1 hour at room temperature. Purify the conjugate on a P-30M gel filtration column (BioRad, 150-4150) in PBS, pH 7.2. Centrifuge the conjugate at 19,000 rpm for 20 minutes to remove aggregates, if present. Determine the degree of labeling by measuring A560 nm/A280 nm.

Example 17

Monitoring Cytosolic Acidification Associated with Ion Channel or Transporter Activation A cytosolically localized version of the pH-sensitive fluorescent dye compound is be a useful indication of proton influx through ion channels or transporters. This may be used for screening of antagonists, agonists, and other modulators of channel/transporter function.

Example 18

Receptor Internalization Assay

The β-2-Adrenergic Receptor (β2AR) is modified to incorporate an epitope tag (VSV-G tag) at the N-terminus. A clonal, stable HEK 293 cell line is established which expresses this receptor (approximately 1.8 pmol/mg cell homogenate). Anti-VSV-G antibody labeled with a pH-sensitive fluorescent dye compound described herein is used to monitor agonist-mediated receptor internalization in these live cells. The assay is performed in the presence and absence of a specific agonist, isoproterenol.

a) Isoproterenol-Induced Receptor Internalization in VSV-G-B2 Adrenergic Cells.

For HEK 293 cells it is preferable to coat plates with poly-D-lysine (Sigma P-6407, 5 mg in 50 ml sterile PBS) prior to seeding the cells. 30-80 µl/well is added and maintained at room temperature for 45 minutes. The coating solution is then aspirated, wash 4× (or more) with 100 µl sterile PBS. Plates can be treated in advance and stored at 4° C. for up to a week (with the final PBS wash still in the wells). Cultured cells can be seeded directly into the wells without first drying the plates. Cultured cells are diluted to ~$1.6 \times 10^5$ cells/ml in complete MEM media (Sigma M2279) containing 200 µg/ml G418. 100 µl of cell suspension is pipetted into each assay well of a poly-D-lysine treated 96-well Packard Viewplate (cell density=16000 cells per well). Plates are then incubated 24-48 hours at 37° C. with 5% $CO_2$. 250 µg lyophilized pH-sensitive fluorescent dye compound labeled anti-VSV-G antibody (PA45407) is reconstituted with 0.5 ml sterile deionized water and mixed thoroughly (stock concentration 0.5 mg/ml). The mixture is centrifuged to remove any precipitate. The compound labeled anti-VSV-G antibody is further diluted to a concentration of 2.5-5 µg/ml using serum-free, phenol red free MEM media. Hoechst 33342 nuclear stain can be added to the 2.5-5 µg/ml antibody solution to a final concentration of 5 µM. Media is subsequently removed from the cells and 100 µl antibody and Hoechst solution is added to each well. The solution is then incubated at room temperature for 15 minutes. 3 µM working dilution of isoproterenol agonist (from 10 mM stock in sterile water; Sigma I5627) is added to the solution and then 50 µl is added to required wells, giving 1 µM final concentration. The wells are incubated at 37° C. for 30 minutes (in a $CO_2$ incubator or on the IN Cell Analyzer 3000). The cells are imaged on an IN Cell Analyzer 3000, IN Cell Analyzer 1000 or a confocal microscope.

b) Internalization of Dye Compound-Labeled Anti-VSV-G Antibody.

HEK 293 cells expressing a VSV-G-β-Adrenergic Receptor are preincubated with anti-VSV-G antibody-dye compound conjugate and stimulated with 1 µM isoproterenol. The cells are imaged using an IN Cell Analyzer 1000. Quantification of the agonist-mediated response is achieved using a granularity algorithm, which defines grains as distinct focal regions within a cell that have pronounced intensity differences from the region of the cell immediately surrounding the grains. The operator can adjust a variety of parameters to control what size and intensity of grain will be counted and analyzed.

c) Internalization of Dye Compound-Labeled Anti-VSV-G Antibody.

HEK VSV-G-β2-Adrenergic Receptor cells are preincubated with pH-sensitive fluorescent dye compound labeled anti-VSV-G antibody and increasing concentrations of isoproterenol (0-1 μM) are then added to the cells. After 30 minutes at 37° C., agonist mediated internalization is analyzed by measuring the increase in pH-sensitive fluorescent dye compound fluorescence using an IN Cell Analyzer 1000 and the granularity analysis algorithm.

Example 19

Detection of Neuronal Cells with a pH-Sensitive Fluorescent Dye Compound

Astroglial feeder layers are established for one week in culture on glass bottomed culture dishes, 35 mm diameter, coated with Poly-L-Lysine. Neurons from embryonic day 18 rat hippocampi are dissociated in culture medium, and seeded onto the feeder layers at a density of 25-35,000 cells per mL, 2 mL per dish, and allowed to grow in neuronal culture medium plus mitotic inhibitors to prevent glial proliferation.

Cells are pre-stained for 15 minutes with 200 ng/mL Hoescht to visualize DNA in the nuclei, and 50 ng/mL calcien AM ester to visualize the cytoplasm by adding 1000×DMSO stocks of these compounds to the cells in complete medium, and then returning them to the cell culture incubator for 15 minutes at 37° C. Cells are removed, and the medium is gently poured off. The cells are immediately placed in 5 μM pH-sensitive fluorescent dye compound, diluted from a 1 mM DMSO stock into normal saline plus 20 mM HEPES and 20 mM glucose, final pH set to 7.4 with NaOH. The cells are incubated in labeling solution for ten minutes at room temperature, and then gently washed twice with saline (above) minus dye for imaging.

Example 20

Phagocytosis of β1 Amyloid Conjugates 1 mg of beta amyloid 1-42 is labeled with a pH-sensitive fluorescent dye compound to yield a dye-beta amyloid conjugate, which is purified by gel filtration to yield a solution of approximately 200 ng/mL with a degree of labeling between 1 and 2 dye molecules per beta amyloid molecule.

2 mL of J774A.1 cells are seeded onto 35 mm, poly-D-lysine coated glass bottom culture dishes at a density of 35,000 cells per mL one day in advance of the study, in serum-free OptiMem culture medium. The dye-beta amyloid conjugate is filtered through a 0.2 micron syringe filter, and 20 microliters of the solution is added to the cells. The culture is returned to the incubator (37° C., 5% $CO_2$) for overnight incubation, and imaged on the following day.

Example 37

Copper-Less Click Reactions Using DIBO-Containing pH-Sensitive Fluorescent Dye Compounds a) Preparation of DIBO-Labeled Dye Compounds:

A solution of pH-sensitive dye compound STP ester (10 mg, 0.0134 mmol) and DIBO amine (Cat. No. C10411, Molecular Probes, Carlsbad, Calif.) (5.0 mg 0.0156 mmol) in DMF (1 mL) is treated with 10 μl of triethylamine (0.072 mmol) and the mixture is stirred at room temperature for 1 hour. All volatile materials are removed by vacuum pump overnight. The crude reaction mixture is dried carefully by vacuum pump and purified by chromatography on a Silica gel column (Biotage, SNAP 10 g $MeOH:CHCl_3$=1:10-1:6) to give a DIBO-dye conjugate.

a) Live Cell Labeling:

Mammalian cells are grown in an appropriate medium at 37° C. in 5% $CO_2$. Supplement the growth medium with an azide-derivatized metabolite (e.g., Click-iT® ManNAz, Life Technologies, Catalog No. C33366) and grow the cells for 2 to 3 days. Wash the cells two times with D-PBS (Life Technologies, Catalog No. 14190-144) containing 1% fetal bovine serum (FBS). Label the azide-modified macromolecules at room temperature in the dark for 1 hour with about 5 to 30 μm DIBO-containing pH-sensitive dye compound in D-PBS containing 1% FBS. Wash the cells four times with D-PBS containing 1% FB S. Fix the cells with 4% formaldehyde in D-PBS for 15 minutes at room temperature. Wash the cells with D-PBS. Optionally, counterstain the cells with an appropriate counterstain, such as Hoechst 33342 and wash the cells. Image the cells.

b) Protein Labeling:

Introduce azide into proteins, e.g., using GalNAz in antibodies using the Click-iT® O-GlcNAc Enzymatic Labeling System (Life Technologies, Catalog No. C33368). Modify the protein-bound azide with DIBO-containing pH-sensitive dye compound. Incubate the protein in TBS with about 5 to 10 μm DIBO-containing pH-sensitive dye compound for at least 1 hour at room temperature. Remove the excess label. Analyze the modified protein.

What is claimed is:

1. A pH-sensitive fluorescent dye compound of structural formula (I):

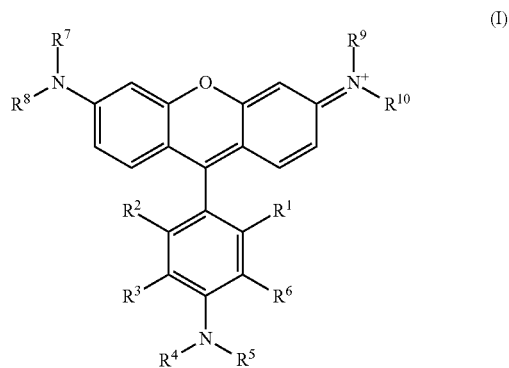

wherein $R^1$ is alkoxy or thioalkyl;

$R^2$ and $R^6$, which may be the same or different, are each independently H, halogen, —$OR^a$, —$SR^a$, —$NR^aR^b$, or an electron donating group;

$R^3$ is —NR'R", wherein R' and R", which may be the same or different, are each independently alkyl or substituted alkyl;

$R^4$ is selected from the group consisting of alkyl and substituted alkyl;

$R^5$ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$, wherein L is a linker, $R_x$ is a reactive group, and $S_c$ is a conjugated substance;

$R^a$ is H, alkyl, or substituted alkyl;
$R^b$ is alkyl or substituted alkyl; and
$R^7$, $R^8$, $R^9$, and $R^{10}$, which may be the same or different, are each independently alkenyl.

2. The compound according to claim 1, wherein
$R^1$ is alkoxy or thioalkyl;
$R^2$ and $R^6$, which may be the same or different, are each independently H or halogen;
$R^3$ is —NR'R", wherein R' and R", which may be the same or different, are each independently alkyl;
$R^4$ is alkyl;
$R^5$ is selected from the group consisting of alkyl; substituted alkyl; alkenyl; substituted alkenyl;
acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and
$R^7$, $R^8$, $R^9$, and $R^{10}$, which may be the same or different, are each independently alkenyl.

3. The compound according to claim 1, wherein
$R^1$ is alkoxy or thioalkyl;
$R^2$ and $R^6$, which may be the same or different, are each independently H, Cl or F;
$R^3$ is —NR'R", wherein R' and R", which may be the same or different, are each independently alkyl;
$R^4$ is alkyl;
$R^5$ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and
$R^7$, $R^8$, $R^9$, and $R^{10}$, which may be the same or different, are each independently alkenyl.

4. The compound according to claim 1, wherein
$R^1$ is alkoxy or thioalkyl;
$R^2$ and $R^6$ are each H;
$R^3$ is —NR'R", wherein R' and R", which may be the same or different, are each independently alkyl;
$R^4$ is alkyl;
$R^5$ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group; -L-$R_x$; and -L-$S_c$; and
$R^7$, $R^8$, $R^9$, and $R^{10}$, which may be the same or different, are each independently alkenyl.

5. The compound according to claim 1, wherein
$R^1$ is methoxy;
$R^2$ and $R^6$ are each H;
$R^3$ is —NR'R", wherein R' and R", which may be the same or different, are each independently methyl or ethyl;
$R^4$ is methyl or ethyl;
$R^5$ is methyl; ethyl; carboxyalkyl; $(CH_2)_nCO(O)R$; $(CH_2)_nC(O)R$; $(CH_2)_nC(O)NHR$; $(CH_2)_nC(O)NRR^c$; wherein n is an integer from 1 to 6, and R and $R^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or $R^d$, wherein $R^d$ is $(CH_2)_nC(O)NHR_x$, wherein n is an integer from 1 to 6, and $R_x$ is a reactive group selected from carboxyl, carboxylester, amide, maleimide, succinimidyl ester (SE), sulfodichlorophenol (SDP) ester, sulfotetrafluorophenol (STP) ester, tetrafluorophenol (TFP) ester, acetoxymethoxy (AM) ester, nitrilotriacetic acid (NTA), aminodextran, DIBO-amine; -L-$R_x$; or -L-$S_c$; and
$R^7$, $R^8$, $R^9$, and $R^{10}$, which may be the same or different, are each independently propenyl.

6. A pH-sensitive fluorescent dye compound of structural formula (II):

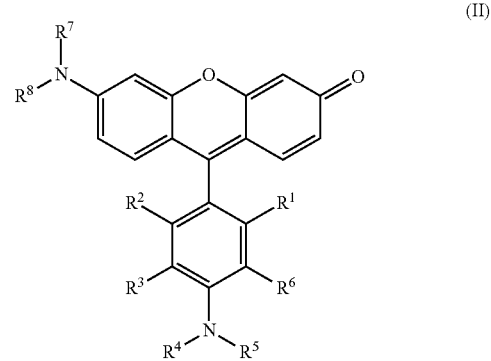

(II)

wherein

R¹ is alkoxy or thioalkyl;

R² and R⁶, which may be the same or different, are each independently H, halogen, —OR$^a$, —SR$^a$, —NR$^a$R$^b$, or an electron donating group;

R³ is —NR'R", wherein R' and R", which may be the same or different, are each independently alkyl or substituted alkyl;

R⁴ is selected from the group consisting of alkyl and substituted alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and R$^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or R$^d$, wherein R$^d$ is $(CH_2)_nC(O)NHR_x$, wherein n is an integer from 1 to 6, and $R_x$ is a reactive group; -L-$R_x$; and -L-$S_c$, wherein L is a linker, $R_x$ is a reactive group, and $S_c$ is a conjugated substance;

R$^a$ is H, alkyl, or substituted alkyl;

R$^b$ is alkyl or substituted alkyl; and

R⁷ and R⁸, which may be the same or different, are each independently alkyl or alkenyl.

7. The compound according to claim 6, wherein

R¹ is alkoxy or thioalkyl;

R² and R⁶, which may be the same or different, are each independently H or halogen;

R³ is —NR'R", wherein R' and R", which may be the same or different, are each independently alkyl;

R⁴ is alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and R$^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or R$^d$, wherein R$^d$ is $(CH_2)_nC(O)NHR_x$, wherein n is an integer from 1 to 6, and $R_x$ is a reactive group; -L-$R_x$; and -L-$S_c$; and R⁷ and R⁸, which may be the same or different, are each independently alkyl or alkenyl.

8. The compound according to claim 6, wherein

R¹ is alkoxy or thioalkyl;

R² and R⁶, which may be the same or different, are each independently H, Cl or F;

R³ is —NR'R", wherein R' and R", which may be the same or different, are each independently alkyl;

R⁴ is alkyl;

R⁵ is selected from the group consisting of alkyl; substituted alkyl; alkenyl; substituted alkenyl; acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and R$^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or R$^d$, wherein R$^d$ is $(CH_2)_nC(O)NHR_x$, wherein n is an integer from 1 to 6, and $R_x$ is a reactive group; -L-$R_x$; and -L-$S_c$; and R⁷ and R⁸, which may be the same or different, are each independently alkyl or alkenyl.

9. The compound according to claim 6, wherein

R¹ is alkoxy or thioalkyl;

R² and R⁶ are each H;

R³ is —NR'R", wherein R' and R", which may be the same or different, are each independently alkyl;

R⁴ is alkyl;

R⁵ is selected from the group consisting of alkyl; substituted alkyl; alkenyl; substituted alkenyl;

acyl; aryl; substituted aryl; carboxyalkyl; heteroaryl; substituted heteroaryl; heterocyclyl; substituted heterocyclyl; alkylcarboxy; alkylalkoxycarbonyl; alkylaminocarbonyl; alkylaryloxycarbonyl; alkylheteroaryl; $(CH_2)_nCO(O)R$; $(CH_2)_nC(O)R$; $(CH_2)_nC(O)NHR$; $(CH_2)_nC(O)NRR^c$, wherein n is an integer from 1 to 6, and R and R$^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or R$^d$, wherein R$^d$ is $(CH_2)_nC(O)NHR_x$, wherein n is an integer from 1 to 6, and $R_x$ is a reactive group; -L-$R_x$; and -L-$S_c$; and R⁷ and R⁸, which may be the same or different, are each independently alkyl or alkenyl.

10. The compound according to claim 6, wherein

R¹ is methoxy;

R² and R⁶ are each H;

R³ is —NR'R", wherein R' and R", which may be the same or different, are each independently methyl or ethyl;

R⁴ is methyl or ethyl;

R⁵ is methyl; ethyl; carboxyalkyl; $(CH_2)_nCO(O)R$; $(CH_2)_nC(O)R$; $(CH_2)_nC(O)NHR$; $(CH_2)_nC(O)NRR^c$; wherein n is an integer from 1 to 6, and R and R$^c$, which may be the same or different, are each independently H, alkyl, substituted alkyl, aryl, substituted aryl, heteroaryl, substituted heteroaryl, substituted amino, alkylaminocarbonyl, aminodextran, amide, a protein, a lipophilic group, or R$^d$, wherein R$^d$ is $(CH_2)_nC(O)NHR_x$, wherein n is an integer from 1 to 6, and $R_x$ is a reactive group selected from carboxyl, carboxylester, amide, maleimide, succinimidyl ester (SE), sulfodichlorophenol (SDP) ester, sulfotetrafluorophenol (STP) ester, tetrafluorophenol (TFP) ester, acetoxymethoxy (AM) ester, nitrilotriacetic acid (NTA), aminodextran, DIBO-amine; -L-$R_x$; or -L-$S_c$; and R⁷ and R⁸, which may be the same or different, are each independently methyl or propenyl.

11. A pH-sensitive dye compound selected from the group consisting of:

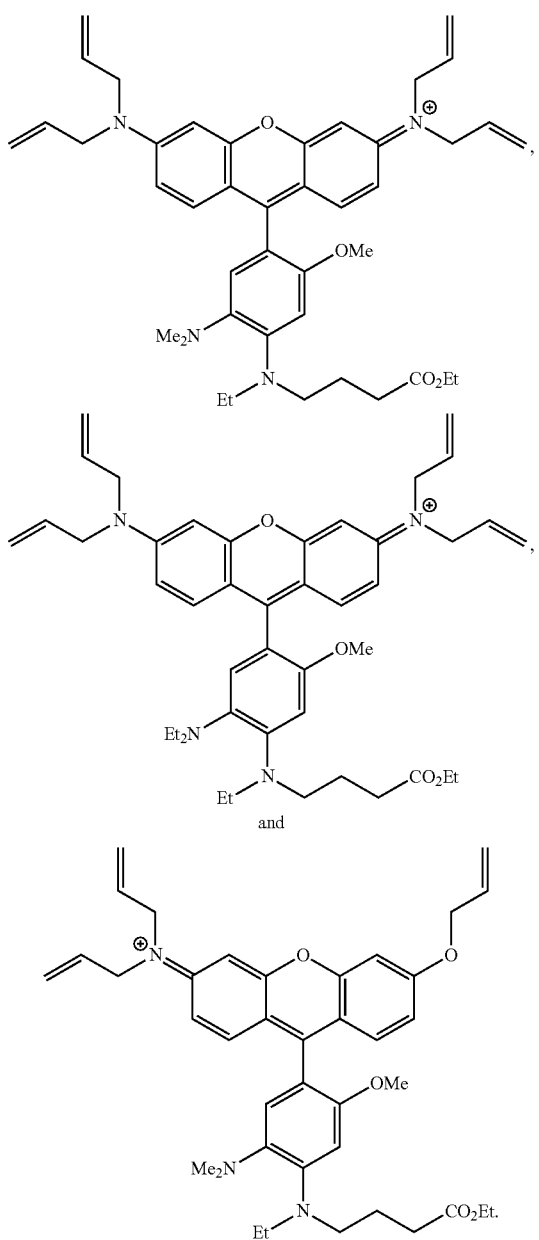

12. A composition for determining the pH of a sample, the composition comprising:
a) one or more of the pH-sensitive fluorescent dye compounds according to claim 1; and
b) a carrier,
wherein the one or more pH-sensitive fluorescent dye compounds are present in an amount effective to detect the pH of the sample.

13. A composition for determining the pH of a sample, the composition comprising:
(a) one or more of the pH-sensitive fluorescent dye compounds according to claim 1; and
(b) an analyte,
wherein the one or more pH-sensitive fluorescent dye compounds are present in an amount effective to detect the pH of the sample.

14. A method for determining the pH of a sample, the method comprising:

(a) contacting the sample with one or more of the pH-sensitive fluorescent dye compounds according to claim 1 to form a contacted sample;
(b) incubating the contacted sample for an appropriate amount of time to form an incubated sample;
(c) illuminating the incubated sample with an appropriate wavelength to form an illuminated sample; and
(d) detecting fluorescent emissions from the illuminated sample;
wherein the fluorescent emissions are used to determine the pH of the sample.

15. A method for monitoring the pH inside a live cell, the method comprising:
(a) contacting the cell with one or more of the pH-sensitive fluorescent dye compounds according to claim 1 to form a contacted cell;
(b) incubating the contacted cell for a sufficient amount of time for the dye compound or composition to enter the cell to form a labeled cell;
(c) illuminating the labeled cell with an appropriate wavelength to form an illuminated cell; and
(d) detecting fluorescent emissions from the illuminated cell;
wherein the fluorescent emissions are used to monitor the pH inside the cell.

16. A method for detecting phagocytosis of a carrier molecule in solution, the method comprising:
(a) conjugating the carrier molecule to one or more of the pH-sensitive fluorescent dye compounds according to claim 1 to form a carrier conjugate;
(b) contacting the carrier conjugate with a cell to form a contacted cell;
(c) incubating the contacted cell to form an incubated solution;
(d) illuminating the incubated solution to form an illuminated solution; and
(e) detecting fluorescent emissions from the illuminated solution;
wherein fluorescent emissions indicate phagocytosis of the carrier molecule.

17. A method for detecting a pH related intracellular process, the method comprising:
(a) contacting one or more of the pH-sensitive fluorescent dye compounds according to claim 1 with a cell to form a contacted cell;
(b) incubating the contacted cell to form an incubated solution;
(c) illuminating the incubated solution to form an illuminated solution; and
(d) detecting fluorescent emissions from the illuminated solution;
wherein increased fluorescent emissions indicates activation of the intracellular process.

18. A method for identifying a target cell in a population of cells, wherein the target cell is differentially labeled relative to neighboring cells within the population, the method comprising:
(a) contacting one or more of the pH-sensitive dye compounds according to claim 1 with the population of cells to form a contacted cell population;
(b) incubating the contacted cell population for a period of time sufficient for the one or more of the pH-sensitive dye compounds to enter the target cell, thereby forming an incubated cell population; and
(c) illuminating the incubated cell population, wherein the target cell is identified by a differential label relative to neighboring cells within the population.

19. A method for diagnosing or detecting a disease in a subject, the method comprising:
- (a) contacting a sample obtained from a subject suspected of having the disease with one or more of the pH-sensitive dye compounds according to claim 1 to form a contacted sample;
- (b) incubating the contacted sample for an appropriate amount of time to form an incubated sample;
- (c) illuminating the incubated sample with an appropriate wavelength to form an illuminated sample; and
- (d) detecting fluorescent emissions from the illuminated sample;

wherein the fluorescent emissions are used to diagnose or detect the disease.

20. A kit for determining the pH of a sample comprising:
- (a) one or more of the pH-sensitive dye compounds according to claim 1;
- (b) one or more containers; and optionally
- (c) instructions for determining the pH of the sample.

* * * * *